US010413600B2

(12) United States Patent
Kopic et al.

(10) Patent No.: US 10,413,600 B2
(45) Date of Patent: *Sep. 17, 2019

(54) SUBCUTANEOUS ADMINISTRATION OF ADAMTS13

(71) Applicants: BAXALTA INCORPORATED, Bannockburn, IL (US); BAXALTA GMBH, Zug (CH)

(72) Inventors: Alexandra Nathalie Kopic, Vienna (AT); Werner Höllriegl, Altenmarkt/Triesting (AT); Barbara Plaimauer, Vienna (AT); Hanspeter Rottensteiner, Vienna (AT); Eva-Maria Muchitsch, Vienna (AT)

(73) Assignees: Baxalta Incorporated, Bannockburn, IL (US); Baxalta GmbH, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/439,154

(22) Filed: Feb. 22, 2017

(65) Prior Publication Data

US 2017/0224785 A1    Aug. 10, 2017

Related U.S. Application Data

(62) Division of application No. 14/210,167, filed on Mar. 13, 2014, now Pat. No. 9,611,467.

(60) Provisional application No. 61/794,659, filed on Mar. 15, 2013.

(51) Int. Cl.
*A61K 38/48* (2006.01)
*C12N 9/64* (2006.01)
*A61K 9/00* (2006.01)
*A61K 9/19* (2006.01)

(52) U.S. Cl.
CPC ........ *A61K 38/4886* (2013.01); *A61K 9/0019* (2013.01); *A61K 9/19* (2013.01); *C12N 9/6489* (2013.01); *C12Y 304/24087* (2013.01)

(58) Field of Classification Search
CPC .... A61K 38/4886; A61K 9/19; A61K 9/0019; C12Y 304/24087; C12N 9/6489
See application file for complete search history.

(56) References Cited

U.S. PATENT DOCUMENTS

2007/0015703 A1  1/2007  Wagner
2011/0229455 A1  9/2011  Matthiessen et al.

FOREIGN PATENT DOCUMENTS

| CN | 1777809       |         | 5/2006  |
|----|---------------|---------|---------|
| CN | 102573792     |         | 7/2012  |
| WO | 199526750     | A1      | 10/1995 |
| WO | 200242441     | A2      | 5/2002  |
| WO | 2003016492    | A2      | 2/2003  |
| WO | 2004095027    |         | 11/2004 |
| WO | 2006133955    | A1      | 12/2006 |
| WO | 2009140140    | A1      | 11/2009 |
| WO | 2011035335    |         | 3/2011  |
| WO | 2012006591    | A1      | 1/2012  |

OTHER PUBLICATIONS

Asada, Y. et al., "Immunohistochemistry of Vascular Lesion in Thrombotic Thrombocytopenic Purpura. With Special Reference to Factor VIII Related Antigen," Thrombosis Research, 1985, 38:469-479.
Berrettini, M. et al., "Subcutaneous Factor IX Administration to Patients With Hemophilia B," Am. J. Hematology, 1994,47(1):61-62.
Chauhan, A.K. et al., "Systemic antithrombotic effects of ADAMTS13," JEM, Mar. 20, D 2006,203(3):767-776.
Chauhan, A.K. et al., "ADAMTS13: a new link between thrombosis and inflammation," JEM, Aug. 11, 2008,205(9):2065-2074.
Demeyer, S.F. et al., "Protective anti-inflammatory effect of ADAMTS13 on myocardial ischemia/reperfusion injury in mice," Blood, Dec. 20, 2012,120(26):5217-5223.
Dent, J.A. et al., "Heterogeneity of plasma von Willebrand Factor Multimers Resulting From Proteolysis of the Constituent Subunit," J Clin Invest., Sep. 1991, 88:774-782.
Dent, J.A. et al., "Identification of a cleavage site directing the immunochemical detection of molecular abnormalities in type IIA von Willebrand factor," Proc Nat! Acad Sci USA, Aug. 1990,87:6306-6310.
Fujikawa, K. et al., "Purification of human von Willebrand factor-cleaving protease and its identification as a new member of the metalloproteinase family," Blood, Sep. 15, 2001, 98(6): 1662-1666.
Furlan, M. et al., "Deficiency of von Willebrand factor-cleaving protease in familial and acquired thrombotic thrombocytopenic purpura," Bai/Mre's Clinical Haematology, Jun. 1998, 11 (2):509-514.
Furlan, M. et al., "Deficient Activity of von Willebrand Factor-Cleaving Protease in Chronic Relapsing Thrombotic Thrombocytopenic Purpura," Blood, May 1, 1997; 89(9):3097-3103.
Furlan, M. et al., "Triplet structure of von Willebrand factor reflects proteolytic degradation of high molecular weight multimers," Proc Nat! Acad Sci USA, Aug. 1993, 90:7503-7507.
Gandhi, C. et al., "ADAMTS13 reduces vascular inflammation and the development of early atherosclerosis in mice," Blood, Mar. 8, 2012, 119(1):2385-2391.
Gerritsen, H.E. et al., "Partial amino acid sequence of purified von Willebrand factor-cleaving protease," Blood, Sep. 15, 2001,98(6):1654-1661.
Jones, G.C., "ADAMTS Proteinases: Potential Therapeutic Targets?" Current Pharmaceutical Biotechnology, 2006, 7:25-31.
Kokame. K. et al., "FRETS-VWF73, a first fluorogenic substrate for ADAMTS13 assay," British Journal of Haematology, 2005,129:93-100.

(Continued)

*Primary Examiner* — Kade Ariani
(74) *Attorney, Agent, or Firm* — Troutman Sanders LLP

(57) ABSTRACT

This invention relates to methods of subcutaneous administration of ADAMTS13 formulations to a treat a disease or condition associated with ADAMTS13 and VWF dysfunction. Furthermore, evidence of the unexpectedly high bioavailability of ADAMTS13 formulations administered subcutaneously is provided herein.

30 Claims, 4 Drawing Sheets

(56) References Cited

OTHER PUBLICATIONS

Larkin, D. et al., "Severe *Plasmodium falciparum* Malaria Is Associated with Circulating Ultra-Large von Willebrand Multimers and ADAMTS13 Inhibition," PLoS Pathogens, Mar. 2009 ;5(3):e1 000349: 1-8.
Levy, G.G. et al., "Mutations in a member of the ADAMTS gene family cause thrombotic thrombocytopenic purpura," Nature, Oct. 4, 2001, 413:488-494.
Moake, J.L. et al., "Unusually Large Plasma Factor VIII:Von Willbrand Factor Multimers in Chronic Relapsing Thrombotic Thrombocytopenic Purpura," The New England Journal of Medicine, Dec. 2, 1982,307(23):1432-1435.
Moake, J.L., "Thrombotic Microangiopathies," N Engl J Med, Aug. 22, 2002,347(8):589-600.
Moake, J.L., "Thrombotic Thrombocytopenic Purpura and the Hemolytic Uremic Syndrome," Arch Pathol Lab Med., Nov. 2002, 126:1430-1433.
Moake, J.L., "Von Willebrand Factor, ADAMTS-13, and Thrombotic Thrombocytopenic Purpura," Seminars in Hematology, Jan. 2004, 41(1):4-14.
Nicholson, A.C. et al., "Functional evolution of ADAMTS genes: Evidence from analyses of phylogeny and gene organization," BMC Evolutionary Biology, Feb. 4, 2005; 5(1): 1-13.
Richter et al., The AAPS Journal, 2012 (Online May 2012), vol. 14, No. 3, p. 559-570.
Sadler, J.E. et al., "Recent Advances in Thrombotic Thrombocytopenic Purpura," Hematology (Am Soc Hematol Educ Program), 2004, pp. 407-423.
Sadler, J.E., "New Concepts in Von Willebrand Disease," Annu. Rev. Med., 2005, 56:173-191.
Scheiflinger, F. et al., "Nonneutralizing IgM and IgG antibodies to von Willebrand factor-cleaving protease (ADAMTS-13) in a patient with thrombotic thrombocytopenic purpura," Blood, Nov. 1, 2003, 102(9):3241-3243.
Siedlecki, CA et al., "Shear-Dependent Changes in the Three-Dimensional Structure of Human von Willebrand Factor," Blood, Oct. 15, 1996,88(8):2939-2950.
Slayter, H. et al., "Native Conformation of Human von Willebrand Protein. Analysis by Electron Microscopy and Quasi-Elastic Light Scattering," J Bioi. Chem., Jul. 15, 1985, 260(14):8559-8563.
Soejima, K. et al., "A Novel Human Metalloprotease Synthesized in the Liver and Secreted into the Blood: Possibly, the von Willebrand Factor-Cleaving Protease?" J. Biochem. 2001; 130:475-480.
Sporn, LA et al., "von Willebrand Factor Released From Weibel-Palade Bodies Binds More Avidly to Extracellular Matrix Than That Secreted Constitutively," Blood, May 1987, 69(5):1531-1534.
Tsai, H-M., "Deficiency of ADAMTS-13 in thrombotic and thrombocytopenic purpura," J. Thromb Haemost. 2003, 1:2038-2040.
Tsai, H-M. et al., "Endothelial Cell-Derived High Molecular Weight von Willebrand Factor is IKAI Converted into the Plasma Multimer Pattern by Granulocyte Proteases," Biochemical and Biophysical; Research Communication, Feb. 15, 1989, 158(3):980-985.
Tsai, H-M. et al., "Multimeric Composition of Endothelial Cell-Derived von Willebrand Factor," Blood, Jun. 1989, 73(8):2074-2076.
Tsai, H-M. et al., "Proteolytic Cleavage of Recombinant Type 2A von Willebrand Factor Mutants R834W and R834Q: Inhibition by Doxycycline and by Monoclonal Antibody VP-1 ," Blood, Mar. 15, 1997; 89(6):1954-1962.
Tsai, H-M. et al., "Antibodies to Von Willebrand Factor-Cleaving Protease in Acute Thrombotic Thrombocytopenic Purpura," N Engl J. Med., 1998; 339(22):1585-1594.
Tsai, H-M., "Von Willebrand factor, ADAMTS13, and thrombotic thrombocytopenic purpura," J Mol Med, 2002, 80:639-647.
Wagner, D. et al., "Von Willebrand Factor and the Endothelium," May Clin Proc, 1991, D 66:621-627.
Wagner, D.o. et al., "Immunolocalization of von Willebrand Protein in Weibel-Palade Bodies of Human Endothelial Cells," J Cell Bioi., Oct. 1982, 95:355-360.
Zheng, X. et al., "Structure of von Willebrand Factor-cleaving Protease (ADAMTS13), a Metalloprotease Involved in Thrombotic Thrombocytopenic Purpura," J. Bioi. Chern., Nov. 2, 2001; 276(44):41059-41063.
Zhao et al., Blood, 2009, vol. 114, No. 15, p. 3329-3334.

SUBCUTANEOUS ADMINISTRATION OF ADAMTS13

CROSS-REFERENCES TO RELATED APPLICATIONS

This application is a divisional of U.S. application Ser. No. 14/210,167, filed Mar. 13, 2014, which claims priority to U.S. Provisional Patent Application Ser. No. 61/794,659 filed Mar. 15, 2013, the disclosure of each are hereby incorporated herein by reference in their entirety for all purposes.

BACKGROUND OF THE INVENTION

The ADAMTS (a disintegrin and metalloproteinase with thrombospondin type I motifs) proteins are a family of metalloproteinases containing number of conserved domains, including a zinc-dependant catalytic domain, a cystein-rich domain, a disintegrin-like domain, and at least one, and in most cases multiple, thrombospondin type I repeats (for review, see Nicholson et al., BMC Evol Biol. 2005 Feb. 4; 5(1):11). These proteins, which are evolutionarily related to the ADAM and MMP families of metalloproteinases (Jones G C, Curr Pharm Biotechnol. 2006 February; 7(1):25-31), are secreted enzymes that have been linked to a number of diseases and conditions including thrombotic thrombocytopenic purpura (TTP) (Moake J L, Semin Hematol. 2004 January; 41(1):4-14), connective tissue disorders, cancers, inflammation (Nicholson et al.), and severe *plasmodium falciparum* malaria (Larkin et al., PLoS Pathog. 2009 March; 5(3):e1000349). Because of these associations, the ADAMTS enzymes have been recognized as potential therapeutic targets for a number of pathologies (Jones G C, Curr Pharm Biotechnol. 2006 February; 7(1): 25-31).

One ADAMTS family member, ADAMTS13, cleaves von Willebrand factor (vWF) between residues Tyr 1605 and Met 1606. Loss of ADAMTS13 activity has been linked to a number of conditions, such as TTP (Moake J L, Semin Hematol. 2004 January; 41(1):4-14), acute and chronic inflammation (Chauhan et al., J Exp Med. 2008 Sep. 1; 205(9):2065-74), and most recently, severe *plasmodium falciparum* malaria (Larkin et al., PLoS Pathog. 2009 March; 5(3):e1000349).

Thrombotic thrombocytopenic purpura (TTP) is a disorder characterized by thrombotic microangiopathy, thrombocytopenia and microvascular thrombosis that can cause various degrees of tissue ischemia and infarction. Clinically, TTP patients are diagnosed by symptoms such as thrombocytopenia, schistocytes (fragments of erythrocytes) and elevated levels of lactate dehydrogenase (Moake J L. Thrombotic microangiopathies. N Engl J Med. 2002; 347: 589-600; Moake J L. von Willebrand factor, ADAMTS-13, and thrombotic thrombocytopenic purpura. Semin Hematol. 2004; 41:4-14; Sadler J E, Moake J L, Miyata T, George J N. Recent advances in thrombotic thrombocytopenic purpura. Hematology (Am Soc Hematol Educ Program). 2004: 407-423; Sadler J E. New concepts in von Willebrand disease. Annu Rev Med. 2005; 56:173-191).

There are two major types of TTP: acquired (noninherited/idopathic) and familial (inherited) (Tsai H M, Lian E C. Antibodies to von Willebrand factor-cleaving protease in acute thrombotic thrombocytopenic purpura. N Engl J. Med. 1998; 339:1585-1594; Furlan M, Lammle B. Deficiency of von Willebrand factor-cleaving protease in familial and acquired thrombotic thrombocytopenic purpura. Baillieres Clin Haematol. 1998; 11:509-514). Genetic mutations in the ADAMTS13 gene cause the familial form of TTP whereas people with acquired TTP do not have the mutations. Rather, acquired TTP is characterized by the production of specific antibodies.

In 1982, Moake et al. found unusually large von Willebrand factor (UL-vWF) multimers in the plasma of the patients with chronic relapsing TTP (Moake J L, Rudy C K, Troll J H, Weinstein M J, Colannino N M, Azocar J, Seder R H, Hong S L, Deykin D. Unusually large plasma factor VIII: von Willebrand factor multimers in chronic relapsing thrombotic thrombocytopenic purpura. N Engl J Med. 1982; 307:1432-1435). The link between UL-vWF and TTP gained support with independent findings by Furlan et al. and Tsai and Lian that most patients suffering from TTP are deficient in a plasma metalloprotease, now known to be ADAMTS13, that cleaves vWF (Furlan M, Robles R, Solenthaler M, Wassmer M, Sandoz P, Laemmle B. Deficient activity of von Willebrand factor-cleaving protease in chronic relapsing thrombotic thrombocytopenic purpura. Blood. 1997; 89:3097-3103; Tsai H M, Sussman, I I, Ginsburg D, Lankhof H, Sixma J J, Nagel R L. Proteolytic cleavage of recombinant type 2A von Willebrand factor mutants R834W and R834Q: inhibition by doxycycline and by monoclonal antibody VP-1. Blood. 1997; 89:1954-1962; Tsai H M, Lian E C. Antibodies to von Willebrand factor-cleaving protease in acute thrombotic thrombocytopenic purpura. N Engl J Med. 1998; 339:1585-1594).

The ADAMTS13 protease is a 190 kDa glycosylated protein produced predominantly by the liver (Levy G G, Nichols W C, Lian E C, Foroud T, McClintick J N, McGee B M, Yang A Y, Siemieniak D R, Stark K R, Gruppo R, Sarode R, Shurin S B, Chandrasekaran V, Stabler S P, Sabio H, Bouhassira E E, Upshaw J D, Jr., Ginsburg D, Tsai H M. Mutations in a member of the ADAMTS gene family cause thrombotic thrombocytopenic purpura. Nature. 2001; 413: 488-494; Fujikawa K, Suzuki H, McMullen B, Chung D. Purification of human von Willebrand factor-cleaving protease and its identification as a new member of the metalloproteinase family. Blood. 2001; 98:1662-1666; Zheng X, Chung D, Takayama T K, Majerus E M, Sadler J E, Fujikawa K. Structure of von Willebrand factor-cleaving protease (ADAMTS13), a metalloprotease involved in thrombotic thrombocytopenic purpura. J Biol Chem. 2001; 276:41059-41063; Soejima K, Mimura N, Hirashima M, Maeda H, Hamamoto T, Nakagaki T, Nozaki C. A novel human metalloprotease synthesized in the liver and secreted into the blood: possibly, the von Willebrand factor-cleaving protease; J Biochem (Tokyo). 2001; 130:475-480; Gerritsen H E, Robles R, Lammle B, Furlan M. Partial amino acid sequence of purified von Willebrand factor-cleaving protease. Blood. 2001; 98:1654-1661).

Mutations in the ADAMTS13 gene have been shown to cause TTP (Levy G G, Nichols W C, Lian E C, Foroud T, McClintick J N, McGee B M, Yang A Y, Siemieniak D R, Stark K R, Gruppo R, Sarode R, Shurin S B, Chandrasekaran V, Stabler S P, Sabio H, Bouhassira E E, Upshaw J D, Jr., Ginsburg D, Tsai H M. Mutations in a member of the ADAMTS gene family cause thrombotic thrombocytopenic purpura. Nature. 2001; 413:488-494). Idiopathic TTP, often caused by autoantibodies inhibiting ADAMTS-13 activity, is a more common disorder that occurs in adults and older children and can recur at regular intervals in 11-36% of patients (Tsai H M, Lian E C. Antibodies to von Willebrand factor-cleaving protease in acute thrombotic thrombocytopenic purpura. N Engl J Med. 1998; 339:1585-1594; Furlan M, Lammle B. Deficiency of von Willebrand factor-cleaving protease in familial and acquired thrombotic thrombocytopenic purpura. Baillieres Clin Haematol. 1998; 11:509-514).

Non neutralizing autoantibodies could also inhibit ADAMTS activity by inducing clearance from circulation (Scheiflinger F, Knobl P, Trattner B, Plaimauer B, Mohr G, Dockal M, Dorner F, Rieger M. Nonneutralizing IgM and IgG antibodies to von Willebrand factor-cleaving protease (ADAMTS-13) in a patient with thrombotic thrombocytopenic purpura. Blood. 2003; 102:3241-3243). Plasma ADAMTS13 activity in healthy adults ranges from 50% to 178% (Moake J L. Thrombotic thrombocytopenic purpura and the hemolytic uremic syndrome. Arch Pathol Lab Med. 2002; 126:1430-1433). In most patients with familial or acquired TTP, plasma ADAMTS13 activity is absent or less than 5% of the normal. Without treatment the mortality rate exceeds 90%, but plasma therapy has reduced mortality to about 20% (Moake J L. Thrombotic thrombocytopenic purpura and the hemolytic uremic syndrome. Arch Pathol Lab Med. 2002; 126:1430-1433).

vWF synthesized in megakaryocytes and endothelial cells is stored in platelet—granules and Weibel-Palade bodies, respectively, as ultra large vWF (UL-vWF) (Moake J L, Rudy C K, Troll J H, Weinstein M J, Colannino N M, Azocar J, Seder R H, Hong S L, Deykin D. Unusually large plasma factor VIII: von Willebrand factor multimers in chronic relapsing thrombotic thrombocytopenic purpura. N Engl J Med. 1982; 307:1432-1435; Wagner D D, Olmsted J B, Marder V J. Immunolocalization of von Willebrand protein in Weibel-Palade bodies of human endothelial cells. J Cell Biol. 1982; 95:355-360; Wagner D D, Bonfanti R. von Willebrand factor and the endothelium. Mayo Clin Proc. 1991; 66:621-627; Sporn L A, Marder V J, Wagner D D. von Willebrand factor released from Weibel-Palade bodies binds more avidly to extracellular matrix than that secreted constitutively. Blood. 1987; 69:1531-1534; Tsai H M, Nagel R L, Hatcher V B, Sussman, I I. Endothelial cell-derived high molecular weight von Willebrand factor is converted into the plasma multimer pattern by granulocyte proteases. Biochem Biophys Res Commun. 1989; 158:980-985; Tsai H M, Nagel R L, Hatcher V B, Sussman, I I. Multimeric composition of endothelial cell-derived von Willebrand factor. Blood. 1989; 73:2074-2076). Once secreted from endothelial cells, these UL-vWF multimers are cleaved by ADAMTS13 in circulation into a series of smaller multimers at specific cleavage sites within the vWF molecule (Tsai H M, Nagel R L, Hatcher V B, Sussman, I I. Endothelial cell-derived high molecular weight von Willebrand factor is converted into the plasma multimer pattern by granulocyte proteases. Biochem Biophys Res Commun. 1989; 158:980-985; Dent J A, Galbusera M, Ruggeri Z M. Heterogeneity of plasma von Willebrand factor multimers resulting from proteolysis of the constituent subunit. J Clin Invest. 1991; 88:774-782; Furlan M, Robles R, Affolter D, Meyer D, Baillod P, Lammle B. Triplet structure of von Willebrand factor reflects proteolytic degradation of high molecular weight multimers. Proc Natl Acad Sci USA. 1993; 90:7503-7507).

ADAMTS13 cleaves at the Tyr842-Met843 bond in the central A2 domain of the mature vWF subunit and requires zinc or calcium for activity (Dent J A, Berkowitz S D, Ware J, Kasper C K, Ruggeri Z M. Identification of a cleavage site directing the immunochemical detection of molecular abnormalities in type IIA von Willebrand factor. Proc Natl Acad Sci USA. 1990; 87:6306-6310). vWF exists in "ball-of-yarn" and filamentous form as seen by electron microscopy (Slayter H, Loscalzo J, Bockenstedt P, Handin R I. Native conformation of human von Willebrand protein. Analysis by electron microscopy and quasi-elastic light scattering. J Biol. Chem. 1985; 260:8559-8563). Furthermore, atomic force microscopy confirms that vWF exits in a globular conformation under static conditions and an unfolded filamentous state after exposure to shear stress (Siedlecki C A, Lestini B J, Kottke-Marchant K K, Eppell S J, Wilson D L, Marchant R E. Shear-dependent changes in the three-dimensional structure of human von Willebrand factor. Blood. 1996; 88:2939-2950). This could occur also in vivo when one end of the vWF filament is anchored to a surface.

Thrombi of TTP patients consist of little fibrin and mainly of vWF and platelets, suggesting vWF-mediated platelet aggregation as a cause of thrombosis (Asada Y, Sumiyoshi A, Hayashi T, Suzumiya J, Kaketani K. Immunohistochemistry of vascular lesion in thrombotic thrombocytopenic purpura, with special reference to factor VIII related antigen. Thromb Res. 1985; 38:469-479). Patients with relapsing TTP have ultra-large multimers in the plasma. The UL-vWF multimers accumulate over time because the persistence of the inhibitor (Anti-ADAMTS 13 Ab) decreases ADAMTS13 activity. The UL-vWF multimers are hyperactive and unfold as a result of shear stress causing platelet aggregation, resulting in intravascular thrombosis (Tsai H M. Von Willebrand factor, ADAMTS13, and thrombotic thrombocytopenic purpura. J Mol Med. 2002; 80:639-647; Tsai H M. Deficiency of ADAMTS-13 in thrombotic and thrombocytopenic purpura. J Thromb Haemost. 2003; 1:2038-2040; discussion 2040-2035).

It is believed that the presence of hyper-reactive UL-vWF multimers in the plasma due to ADAMTS13 deficiency could be associated with an increased risk of arterial thrombosis linked to coronary heart disease. Furthermore, ADAMTS13 has been linked to cerebral infarction, myocardial infarction, ischemic/reperfusion injury, deep vein thrombosis, and disseminated intravascular coagulation. Accordingly, there is a need for pharmaceutical formulations of ADAMTS13 proteins suitable for the treatment of various diseases and conditions associated with ADAMTS13 and VWF dysfunction.

However, pharmaceutical formulations comprising very large and labile molecules such as ADAMTS13 can generally only be administered intravenously. This is because such pharmaceutical formulations normally exhibit a very low bioavailablity due to insufficient absorption and severe degradation when given subcutaneously, intramuscularly, and intradermally. Accordingly, due to the low bioavailability, large and labile proteins are normally administered intravenously to provide direct availability to the blood stream.

While ADAMTS13 can be administered intravenously to treat various diseases and conditions associated with ADAMTS13 and VWF dysfunction, it is inconvenient and not easy for patients to handle. Particularly, ADAMTS13 formulations are often administered regularly throughout a patient's life. For example, patients with familial (inherited) TTP begin treatment with intravenous ADAMTS13 in their first year of life. Accordingly, it would be advantageous to subcutaneously administer a pharmaceutical composition of ADAMTS13. However, low bioavailabilities of subcutaneously administered large and labile protein formulations has prevented the development of such subcutaneous formulations.

Previous studies have reported that certain coagulation factors VII, VIII, and IX that are suitable for subcutaneous administration. For example, PCT/SE95/00348 reports a Factor VIII formulation that is highly purified that contains additives such as hydrolyzed gelatin, hyaluronic acid, and soybean oil emulsion. The purification and additives allowed for the Factor VIII formulation to be highly concentrated. This highly concentrated formulation resulted in a bioavailability of at least about 15% and suitably at least about 30% after subcutaneous, intramuscular, or intradermal administration compared to the bioavailability after intravenous administration. However, 15-30% bioavailability of subcutaneous administration compared to intravenous administration is still very low and would not be effective at treating ADAMTS13 disorders.

Furthermore, the prior studies do not provide a general principle for subcutaneous administration of large and labile proteins. Rather, prior studies present evidence of that it is subcutaneous pharmaceutical compositions of large and labile proteins are difficult to prepare because the compositions lack the requisite bioavailability for subcutaneous administration.

Described herein is a method of subcutaneously administering an ADAMTS13 formulation to a treat a disease or condition associated with ADAMTS13 and VWF dysfunction. Specifically, evidence of the unexpectedly high bioavailability, up to approximately 70%, of ADAMTS13 formulations administered subcutaneously is provided herein.

BRIEF SUMMARY OF THE INVENTION

In one aspect, the present disclosure provides a method for treating a blood clotting disorder in a mammal, the method comprising subcutaneously administering a therapeutically effective amount of a composition comprising isolated ADAMTS13 to the mammal in need thereof, wherein the therapeutically effective amount of ADAMTS13 comprises 20-4000 activity units per kilogram.

In one embodiment of the methods provided herein, the clotting disorder is selected from the group consisting of inherited TTP, acquired TTP, cerebral infarction, myocardial infarction. ischemic/reperfusion injury, deep vein thrombosis, and sepsis-related disseminated intravascular coagulation.

In one embodiment of the methods provided herein, the bioavailability of the ADAMTS13 after subcutaneous administration is 50-80% as compared to intravenous administration normalized for the same dose.

In one embodiment of the methods provided herein, the bioavailability of the ADAMTS13 after subcutaneous administration is at least 50% as compared to intravenous administration normalized for the same dose.

In one embodiment of the methods provided herein, the bioavailability of the ADAMTS13 after subcutaneous administration is at least 55% as compared to intravenous administration normalized for the same dose.

In one embodiment of the methods provided herein, the bioavailability of the ADAMTS13 after subcutaneous administration is at least 60% as compared to intravenous administration normalized for the same dose.

In one embodiment of the methods provided herein, the bioavailability of the ADAMTS13 after subcutaneous administration is at least 65% as compared to intravenous administration normalized for the same dose.

In one embodiment of the methods provided herein, the bioavailability of the ADAMTS13 after subcutaneous administration is at least 70% as compared to intravenous administration normalized for the same dose.

In one embodiment of the methods provided herein, the bioavailability of the ADAMTS13 after subcutaneous administration is at least 75% as compared to intravenous administration normalized for the same dose.

In one embodiment of the methods provided herein, the bioavailability of the ADAMTS13 after subcutaneous administration is at least 80% as compared to intravenous administration normalized for the same dose.

In one embodiment of the methods provided herein, the bleeding episode is inherited TTP.

In one embodiment of the methods provided herein, the therapeutically effective amount comprises at least 20-160 activity units per kilogram.

In one embodiment of the methods provided herein, the bleeding episode is acquired TTP.

In one embodiment of the methods provided herein, the therapeutically effective amount comprises at least 40-2000 activity units per kilogram.

In one embodiment of the methods provided herein, the bleeding episode is cerebral infarction and/or ischemia reperfusion injury.

In one embodiment of the methods provided herein, the therapeutically effective amount comprises at least 40-4000 activity units per kilogram In one embodiment of the methods provided herein, the bleeding episode is myocardial infarction and/or ischemia reperfusion injury.

In one embodiment of the methods provided herein, the therapeutically effective amount comprises at least 40-2000 activity units per kilogram.

In one embodiment of the methods provided herein, the ADAMTS13 is administered in a single bolus injection, monthly, every two weeks, weekly, twice a week, daily, every 12 hours, every 8 hours, every six hours, every four hours, or every two hours.

In one embodiment of the methods provided herein, the ADAMTS13 is recombinant.

In one embodiment of the methods provided herein, the ADAMTS13 is plasma derived.

In one embodiment of the methods provided herein, the mammal is a human.

In one embodiment of the methods provided herein, the composition is a stable aqueous solution ready for administration.

In one embodiment of the methods provided herein, the composition is lyophilized.

In one embodiment of the methods provided herein, the composition is reconstituted with a pharmaceutically acceptable vehicle suitable for injection.

In one aspect, the present disclosure provides a method for treating a bleeding episode in a mammal, the method comprising subcutaneously administering a therapeutically effective amount of a composition comprising isolated ADAMTS13 to the mammal in need thereof, wherein the therapeutically effective amount of ADAMTS13 comprises at least 120-300% of the amount of a standard intravenous dose for a specific indication as measured in activity units per kilogram.

In one embodiment of the methods provided herein, the specific indication is inherited TTP and the standard intravenous dose is 10-80 activity units per kilogram.

In one embodiment of the methods provided herein, the specific indication is acquired TTP and the standard intravenous dose is 20-1000 activity units per kilogram.

In one embodiment of the methods provided herein, the specific indication is myocardial infarction and/or ischemia reperfusion injury and the standard intravenous dose is 20-2000 activity units per kilogram.

In one embodiment of the methods provided herein, the specific indication is cerebral infarction and/or ischemia reperfusion injury and the standard intravenous dose is 20-2000 activity units per kilogram.

In one embodiment of the methods provided herein, the bioavailability of the ADAMTS13 after subcutaneous administration is 50-80% as compared to intravenous administration normalized for the same dose.

In one embodiment of the methods provided herein, the bioavailability of the ADAMTS13 after subcutaneous administration is at least 50% as compared to intravenous administration normalized for the same dose.

In one embodiment of the methods provided herein, the bioavailability of the ADAMTS13 after subcutaneous administration is at least 55% as compared to intravenous administration normalized for the same dose.

In one embodiment of the methods provided herein, the bioavailability of the ADAMTS13 after subcutaneous administration is at least 60% as compared to intravenous administration normalized for the same dose.

In one embodiment of the methods provided herein, the bioavailability of the ADAMTS13 after subcutaneous administration is at least 65% as compared to intravenous administration normalized for the same dose.

In one embodiment of the methods provided herein, the bioavailability of the ADAMTS13 after subcutaneous administration is at least 70% as compared to intravenous administration normalized for the same dose.

In one embodiment of the methods provided herein, the bioavailability of the ADAMTS13 after subcutaneous administration is at least 75% as compared to intravenous administration normalized for the same dose.

In one embodiment of the methods provided herein, the bioavailability of the ADAMTS13 after subcutaneous administration is at least 80% as compared to intravenous administration normalized for the same dose.

In one embodiment of the methods provided herein, the ADAMTS13 is administered in a single bolus injection, monthly, every two weeks, weekly, twice a week, daily, every 12 hours, every 8 hours, every six hours, every four hours, or every two hours.

In one embodiment of the methods provided herein, the ADAMTS13 is recombinant.

In one embodiment of the methods provided herein, the ADAMTS13 is plasma derived.

In one embodiment of the methods provided herein, the mammal is a human.

In one embodiment of the methods provided herein, the composition is a stable aqueous solution ready for administration.

In one embodiment of the methods provided herein, the composition is lyophilized.

In one embodiment of the methods provided herein, the composition is reconstituted with a pharmaceutically acceptable vehicle suitable for injection.

DETAILED DESCRIPTION OF THE INVENTION

I. Introduction

Figure 1:
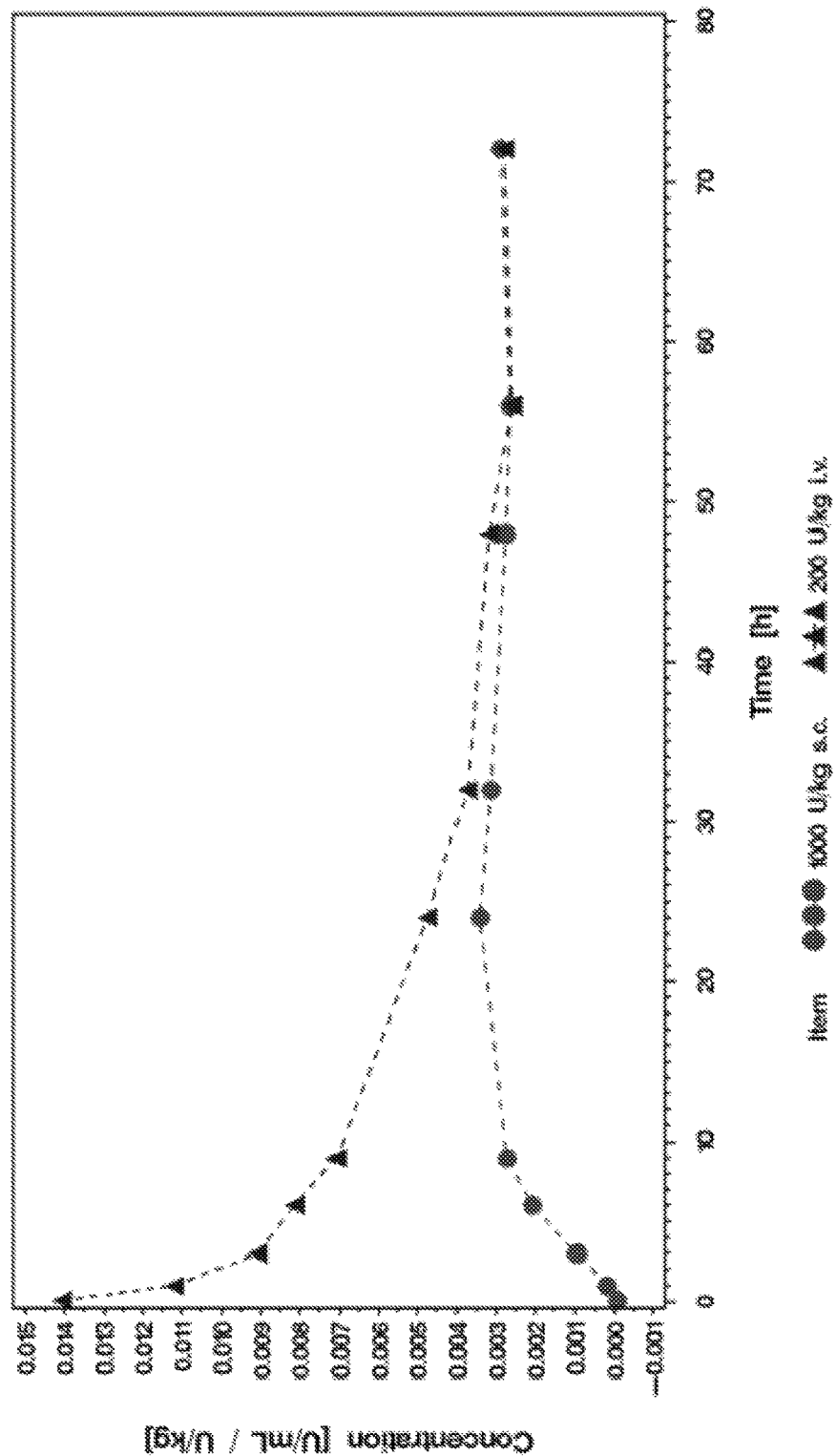
FIG. 1 shows the mean plasma concentrations of ADAMTS13 activity. Median $T_{max}$ after s.c. administration was 24 h for ADAMTS13 activity.

ADAMTS13 (A13) is a plasma metalloprotease which cleaves von Willebrand factor (VWF) multimers and down regulates their activity in platelet aggregation. ADAMTS13 is associated clotting disorders such as inherited thrombotic thrombocytopenic purpura (TTP), acquired TTP, cerebral infarction, myocardial infarction, ischemic/reperfusion injury, deep vein thrombosis, and disseminated intravascular coagulation (DIC) such as sepsis-related DIC.

Current treatment of these clotting disorders involves intravenous administration of ADAMTS13 formulations. Treatment is currently limited to intravenous administration because ADAMTS13 is a large protein and large proteins are generally not stable in formulations with high bioavailabilities suitable for subcutaneous administration. The mature ADAMTS13 has a calculated molecular mass of about 145 kDa whereas purified plasma-derived ADAMTS13 has an apparent molecular mass of about 180 kDa probably due to post-translational modifications consisting with present consensus sequences for 10 potential N-glycosylation sites, and several O-glycosylation sites and one C-mannosylation site in the TSP1 repeats.

Proteins and molecules that are large and labile such as ADAMTS13, are generally limited to intravenous administration due to the low bioavailability of the formulations when administered subcutaneously. For example, previous studies report that Factor VIII, a 170 to 300 kDa protein, is typically administered intravenously because Factor VIII formulations normally exhibit a very low bioavailability due to insufficient absorption and severe degradation when administered subcutaneously, intramuscularly or intradermally. See PCT/SE95/00348.

For example, it has been reported that Factor VIII concentrate injected intramuscularly yielded a maximum circulating level of only 1.4% of the normal plasma level with and without sodium citrate as an additive to used to prevent degradation and increase absorption (Pool et al, New England J. Medicine, vol. 275, no. 10, p. 547-548, 1966). The studies further revealed that there was no significant difference in the activity recovered in the circulation regardless of whether such citrate was added to the preparation. In a later study, a high-purity factor VIII was administered intramuscularly to haemophilic dogs and human volunteers (Johnson et al, Br. J. Hematology, vol. 21, p. 21-41, 1971). Although, the doses were much larger than used by Pool et al., neither the dogs nor the human volunteers showed a significant rise in plasma factor VIII levels. In fact, the plasma factor VIII concentration in the haemophilic human volunteers remained below 1% of the normal plasma level, i.e. the severe haemophilia A prevailed even after administration in the absence of additives increasing the bioavailability.

There has been some success at subcutaneous delivery of small proteins such as Factor IX that do not degrade and aggregate like large, labile proteins such as Factor VIII and ADAMTS13. For example, subcutaneous administration of factor IX without additives is known from Berettini et al., "Subcutaneous factor IX administration to patients with hemophilia B," Am. J. Hematology, 47(1):61-62, 1994. However, even Factor IX, which is only 56 kDa, exhibited poor and very slow transport into the circulation.

Due to the low bioavailability of proteins such as Factors VIII and IX as described above, methods of subcutaneous delivery of large and labile proteins are not generally pursued. Rather, such proteins are normally given intravenously so that the formulation is directly available in the blood stream. It would however be advantageous if a medicament could be given subcutaneously because subcutaneous administration is a minimally invasive mode of administration. Subcutaneous administration is also the most versatile mode of administration that can be used for short term and long term therapies. Subcutaneous administration can be performed by injection or by implantation of a sustained or timed release device beneath the surface of the skin. The site of the injection or device can be rotated when multiple injections or devices are needed.

Accordingly, subcutaneous formulations much easier to handle for the patient, especially since the formulation may have to be taken regularly during the whole life (e.g., starting as early as a child's first year of life). Furthermore, the easy and speed of subcutaneous delivery allows increased patient compliance and quicker access to medication when needed. Thus, there is a benefit and need for subcutaneous formulations of ADAMTS13.

The present invention is based on the unexpected discovery of a successful method of subcutaneously administering liquid and lyophilized formulations of purified ADAMTS proteins.

II. Definitions

As used herein, "ADAMTS13" or "A13" refer to a metalloprotease of the ADAMTS (a disintegrin and metalloproteinase with thrombospondin type I motifs) family that cleaves von Willebrand factor (vWF) between residues Tyr 1605 and Met 1606. In the context of the present invention, an "ADAMTS13 protein" embraces any ADAMTS13 protein, for example, ADAMTS13 from a mammal such as a primate, human (NP620594), monkey, rabbit, pig, bovine (XP610784), rodent, mouse (NP001001322), rat (XP342396), hamster, gerbil, canine, feline, frog (NP001083331), chicken (XP415435), and biologically active derivatives thereof. As used herein, "ADAMTS13 proteins" refer to recombinant and plasma derived ADAMTS13 proteins. Mutant and variant ADAMTS13 proteins having activity are also embraced, as are functional fragments and fusion proteins of the ADAMTS13 proteins. Furthermore, the ADAMTS13 proteins of the invention may further comprise tags that facilitate purification, detection, or both. The ADAMTS13 proteins described herein may further be modified with a therapeutic moiety or a moiety suitable imaging in vitro or in vivo.

Human ADAMTS13 proteins include, without limitation, polypeptides comprising the amino acid sequence of GenBank accession number NP 620594 or a processed polypeptide thereof, for example a polypeptide in which the signal peptide (amino acids 1 to 29) and/or propeptide (amino acids 30-74) have been removed. Many natural variants of human ADAMTS13 are known in the art, and are embraced by the formulations of the present invention, some of which include mutations selected from R7W, V88M, H96D, R102C, R193W, T196I, H234Q, A250V, R268P, W390C, R398H, Q448E, Q456H, P457L, P475S, C508Y, R528G, P618A, R625H, I673F, R692C, A732V, E740K, A900V, S903L, C908Y, C951G, G982R, C1024G, A1033T, R1095W, R1095W, R1123C, C1213Y, T1226I, G1239V, and R1336W. Additionally, ADAMTS13 proteins include natural and recombinant proteins that have been mutated, for example, by one or more conservative mutations at a nonessential amino acid. Preferably, amino acids essential to the enzymatic activity of ADAMTS13 will not be mutated. These include, for example, residues known or presumed to be essential for metal binding such as residues 83, 173, 224, 228, 234, 281, and 284, and residues found in the active site of the enzyme, e.g., residue 225. Similarly, in the context of the present invention, ADAMTS13 proteins include alternate isoforms, for example, isoforms lacking amino acids 275 to 305 and/or 1135 to 1190 of the full-length human protein.

Likewise, ADAMTS13 proteins may be further modified, for example, by post-translational modifications (e.g., glycosylation at one or more amino acids selected from human residues 142, 146, 552, 579, 614, 667, 707, 828, 1235, 1354, or any other natural or engineered modification site) or by ex vivo chemical or enzymatic modification, including without limitation, glycosylation, modification by water soluble polymer (e.g., PEGylation, sialylation, HESylation, etc.), tagging, and the like.

As used herein, "blood clotting disorder" is defined as a disorder that includes dysfunctional platelet recruitment as well as dysfunctional neutrophil recruitment. Non-limiting examples of "blood clotting disorders" include inherited thrombotic thrombocytopenic purpura (TTP), acquired TTP, cerebral infarction, myocardial infarction, ischemic/reperfusion injury, deep vein thrombosis, and disseminated intravascular coagulation (DIC) such as sepsis-related DIC.

As used herein, "one unit of ADAMTS13 activity" is defined as the amount of activity in 1 ml of pooled normal human plasma, regardless of the assay being used. For example, one unit of ADAMTS13 FRETS-VWF73 activity is the amount of activity needed to cleave the same amount of FRETS-VWF73 substrate (Kokame et al., Br J Haematol. 2005 April; 129(1):93-100) as is cleaved by one ml of pooled normal human plasma. Additional activity assays can also be used to determine the activity of one unit of ADAMTS13. For example, direct ADAMTS13 activity assays can be performed to detect the cleavage of either full-length VWF molecules or VWF fragments using SDS agrose gel electrophoresis and indirect detection of ADAMTS13 activity can be detected with collagen binding assays.

As used herein, the terms "ADAMTS13" and "biologically active derivative", respectively, also include polypeptides obtained via recombinant DNA technology. Alternatively, ADAMTS13 can also refer to the plasma derived ADAMTS13 purified from pooled human blood. The recombinant ADAMTS13 ("rADAMTS13"), e.g. recombinant human ADAMTS13 ("r-hu-ADAMTS13"), may be produced by any method known in the art. One specific example is disclosed in WO 02/42441 which is incorporated herein by reference with respect to the method of producing recombinant ADAMTS13. This may include any method known in the art for (i) the production of recombinant DNA by genetic engineering, e.g. via reverse transcription of RNA and/or amplification of DNA, (ii) introducing recombinant DNA into prokaryotic or eukaryotic cells by transfection, i.e. via electroporation or microinjection, (iii) cultivating said transformed cells, e.g. in a continuous or batchwise manner, (iv) expressing ADAMTS13, e.g. constitutively or upon induction, and (v) isolating said ADAMTS13, e.g. from the culture medium or by harvesting the transformed cells, in order to (vi) obtain substantially purified recombinant ADAMTS13, e.g. via anion exchange chromatography or affinity chromatography. The term "biologically active derivative" includes also chimeric molecules such as, e.g. ADAMTS13 (or a biologically active derivative thereof) in combination with Ig, in order to improve the biological/pharmacological properties such as, e.g. half life of ADAMTS13 in the circulation system of a mammal, particularly human. The Ig could have also the site of binding to an optionally mutated Fc receptor.

As used herein, the term "thrombus" refers to a blood clot, especially a platelet-comprising blood clot, a microthrombus, and/or an embolus. Said thrombus may be attached to an arterial or venous blood vessel or not, and may partially or completely block the blood flow in an arterial or venous blood vessel.

As used herein, a "therapeutically effective amount or dose" or "sufficient amount or dose" refers to a dose that produces effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

As used herein, a "physiological concentration" of salt refers to a salt concentration of between about 100 mM and about 200 mM of a pharmaceutically acceptable salt. Non-limiting examples of pharmaceutically acceptable salts include, without limitation, sodium and potassium chloride, sodium and potassium acetate, sodium and potassium citrate, sodium and potassium phosphate.

As used herein, a "sub-physiological concentration" of salt refers to a salt concentration of less than about 100 mM of a pharmaceutically acceptable salt. In preferred embodiments, a sub-physiological concentration of salt is less than about 80 mM of a pharmaceutical salt. In another preferred embodiment, a sub-physiological concentration of salt is less than about 60 mM of a pharmaceutical salt.

As used herein, the term "about" denotes an approximate range of plus or minus 10% from a specified value. For instance, the language "about 20%" encompasses a range of 18-22%. As used herein, about also includes the exact amount. Hence "about 20%" means "about 20%" and also "20%."

III. ADAMTS13 Compositions and Formulation

In one aspect, the present invention provides stabilized formulations of plasma derived ADAMTS13 and recombinant ADAMTS13 (rADAMTS13) proteins as described in U.S. Patent Application Publication No. 2011/0229455. In other embodiments, the formulations provided herein retain significant ADAMTS13 activity when stored for extended periods of time. In yet other embodiments, the formulations of the invention reduce or retard dimerization, oligomerization, and/or aggregation of an ADAMTS13 protein.

In one embodiment, the present invention provides formulations of ADAMTS13 comprising a therapeutically effective amount or dose of an ADAMTS13 protein, a sub-physiological to physiological concentration of a pharmaceutically acceptable salt, a stabilizing concentration of one or more sugars and/or sugar alcohols, a non-ionic surfactant, a buffering agent providing a neutral pH to the formulation, and optionally a calcium and/or zinc salt. Generally, the stabilized ADAMTS13 formulations provided herein are suitable for pharmaceutical administration. In a preferred embodiment, the ADAMTS13 protein is human ADAMTS13 or a biologically active derivative or fragment thereof as described in U.S. Patent Application Publication No. 2011/0229455.

In certain embodiments, the ADAMTS13 formulations are liquid formulations. In other embodiments, the ADAMTS13 formulations are lyophilized formulations that are lyophilized from a liquid formulation as described in U.S. Patent Application Publication No. 2011/0229455. In certain embodiments of the formulations provided herein, the ADAMTS13 protein is a human ADAMTS13 or recombinant human ADAMTS13, or a biologically active derivative or fragment thereof as described in U.S. Patent Application Publication No. 2011/0229455.

In certain embodiments, ADAMTS13 is provided in a therapeutically effective dose between about 0.05 mg/mL and about 10 mg/mL. In other embodiments, ADAMTS13 is present at a concentration of between about 0.1 mg/mL and about 10 mg/mL. In yet other embodiments, ADAMTS13 is present at a concentration of between about 0.1 mg/mL and about 5 mg/mL. In another embodiment, ADAMTS13 is present at a concentration of between about 0.1 mg/mL and about 2 mg/mL. In yet other embodiments, ADAMTS13 may be present at about 0.01 mg/mL, or at about 0.02 mg/mL, 0.03 mg/mL, 0.04 mg/mL, 0.05 mg/mL, 0.06 mg/mL, 0.07 mg/mL, 0.08 mg/mL, 0.09 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.5 mg/mL, 3.0 mg/mL, 3.5 mg/mL, 4.0 mg/mL, 4.5 mg/mL, 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10.0 mg/mL, or a higher concentration. In one embodiment, the concentration of a relatively pure ADAMTS13 formulation may be determined by spectroscopy (i.e., total protein measured at A280) or other bulk determination (e.g., Bradford assay, silver stain, weight of a lyophilized powder, etc.). In other embodiments, the concentration of ADAMTS13 may be determined by an ADAMTS13 ELISA assay (e.g., mg/mL antigen).

In yet other embodiments, the concentration of ADAMTS13 in a formulation provided by the present invention may be expressed as a level of enzymatic activity. For example, in one embodiment an ADAMTS13 formulation may contain between about 10 units of FRETS-VWF73 activity and about 10,000 units of FRETS-VWF73 activity or other suitable ADAMTS13 enzymatic unit (IU). In other embodiments, the formulation may contain between about 20 units of FRETS-VWF73 ($U_{FV73}$) activity and about 8,000 units of FRETS-VWF73 activity, or between about 30 $U_{FV73}$ and about 6,000 $U_{FV73}$, or between about 40 $U_{FV73}$ and about 4,000 $U_{FV73}$, or between about 50 $U_{FV73}$ and about 3,000 $U_{FV73}$, or between about 75 $U_{FV73}$ and about 2,500 $U_{FV73}$, or between about 100 $U_{FV73}$ and about 2,000 $U_{FV73}$, or between about 200 $U_{FV73}$ and about 1,500 $U_{FV73}$, or between about other ranges therein. In a preferred embodiment, an ADAMTS13 formulation provided herein contains between about 20 and about 10,000. $U_{FV73}$. In certain embodiments, a formulation contains about 10 units of FRETS-VWF73 activity, or about 20, 30, 40, 50, 60, 70, 80, 90, 100, 150, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000 or more units of FRETS-VWF73 activity.

Similarly, in certain embodiments, the concentration of ADAMTS13 may be expressed as an enzymatic activity per unit volume, for example, ADAMTS13 enzymatic units per mL (IU/mL). For example, in one embodiment an ADAMTS13 formulation may contain between about 10 IU/mL and about 10,000 IU/mL. In other embodiments, the formulation may contain between about 20 IU/mL and about 10,000 IU/mL, or between about 20 IU/mL and about 8,000 IU/mL, or between about 30 IU/mL and about 6,000 IU/mL, or between about 40 IU/mL and about 4,000 IU/mL, or between about 50 IU/mL and about 3,000 IU/mL, or between about 75 IU/mL and about 2,500 IU/mL, or between about 100 IU/mL and about 2,000 IU/mL, or between about 200 IU/mL and about 1,500 IU/mL, or between about other ranges therein. In a preferred embodiment, an ADAMTS13 formulation provided herein contains between about 150 IU/mL and about 600 IU/mL. In another preferred embodiment, an ADAMTS13 formulation provided herein contains between about 100 IU/mL and about 1,000 IU/mL. In certain embodiments, a formulation contains about 10 IU/mL, or about 20, 30, 40, 50, 60, 70, 80, 90, 100, 150, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000 or more IU/mL.

In some embodiments, the ADAMTS13 formulations provided herein may further comprise one or more pharmaceutically acceptable excipients, carriers, and/or diluents as described in U.S. Patent Application No. 20110229455. Furthermore, in one embodiment, the ADAMTS13 formulations provided herein will have a tonicity in a range described in as described in U.S. Patent Application Publication No. 2011/0229455.

In further embodiments, the present invention provides formulations of ADAMTS13 comprising the exemplary formulations described in Section III ("ADAMTS13 Compositions and Formulations") of U.S. Patent Application Publication No. 2011/0229455.

In certain embodiments ADAMTS13 formulations are produced and comprise the additives. The methods of ADAMTS13 production and compositions thereof as described in U.S. Patent Application Publication No. 2011/0229455, Sections IV and V, are incorporated herein by reference.

IV. Methods of Treatment

The formulations described herein can be subcutaneously administered for therapeutic or prophylactic treatments. Generally, for therapeutic applications, formulations are administered to a subject with a disease or condition associated with ADAMTS13 or VWF dysfunction or otherwise in need thereof, in a "therapeutically effective dose." Formulations and amounts effective for these uses will depend upon the severity of the disease or condition and the general state of the patient's health. Single or multiple administrations of the formulations may be administered depending on the dosage and frequency as required and tolerated by the patient.

A "patient" or "subject" for the purposes of the present invention includes both humans and other animals, particularly mammals. Thus the compositions, formulations, and methods are applicable to both human therapy and veterinary applications. In a particular embodiment the patient is a mammal, and in one embodiment, is a human. Other known treatments and therapies for conditions associated with ADAMTS13 or VWF dysfunction can be used in combination with the formulations and methods provided by the invention.

In certain embodiments, the subcutaneous ADAMTS13 formulation is administered by subcutaneous injection. In specific embodiments, the subcutaneous ADAMTS13 formulation is subcutaneously injected into the same site of a patient (e.g., administered to the upper arm, anterior surface of the thigh, lower portion of the abdomen, or upper back) for repeat or continuous injections. In other embodiments, the subcutaneous ADAMTS13 formulation is subcutaneously injected into the different or rotating sites of a patient. In certain embodiments, the subcutaneous ADAMTS13 formulation is administered by subcutaneously implanted device. In certain embodiments, the implanted device provides a timed release of an ADAMTS13 formulation. In certain embodiments, the implanted device provides a continuous release of an ADAMTS13 formulation.

In certain embodiments, an ADAMTS13 formulation described herein is used for the treatment and prophylaxis of ADAMTS13 and vWF dysfunction. In certain embodiments, an ADAMTS13 formulation described herein is used for the treatment and prophylaxis of thrombotic diseases and conditions. In certain embodiments, an ADAMTS13 formulation described herein is used for the treatment and prophylaxis of an infarction.

In one embodiment, ADAMTS13 is administered at a dose of from 20 $U_{FV73}$/kg body weight to 4000 $U_{FV73}$/kg body weight. In one embodiment, ADAMTS13 is administered at a dose of from 20 $U_{FV73}$/kg body weight to 2000 $U_{FV73}$/kg body weight. In one embodiment, ADAMTS13 is administered at a dose of from 20 $U_{FV73}$/kg body weight to 1000 $U_{FV73}$/kg body weight. In one embodiment, ADAMTS13 is administered at a dose of from 20 $U_{FV73}$/kg body weight to 500 $U_{FV73}$/kg body weight. In one embodiment, ADAMTS13 is administered at a dose of from 20 $U_{FV73}$/kg body weight to 200 $U_{FV73}$/kg body weight. In one embodiment, ADAMTS13 is administered at a dose of from 20 $U_{FV73}$/kg body weight to 100 $U_{FV73}$/kg body weight. In one embodiment, ADAMTS13 is administered at a dose of from 40 $U_{FV73}$/kg body weight to 200 $U_{FV73}$/kg body weight. In one embodiment, ADAMTS13 is administered at a dose of from 40 $U_{FV73}$/kg body weight to 100 $U_{FV73}$/kg body weight. In other embodiments, ADAMTS13 is administered at about 20 $U_{FV73}$/kg body weight, 30, 40, 50, 60, 70, 80, 90, 100, 150, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000 $U_{FV73}$/kg body weight, or at an intermediate concentration or concentration range thereof.

Generally, the dose of ADAMTS13 administered to a mammal will depend upon, among other factors, the disease or condition being treated, the species of the mammal, the age of the mammal, and the overall health of the mammal. The skilled person will readily be able to translate dosages between different mammals, for example from a mouse dose to a human dose. One means for extrapolating a human dose from an animal dose includes the use of body surface area, which is known to correlate well with several metabolic parameters, e.g., blood volume, circulating plasma, and renal function, in diverse mammals. Thus, a conversion factor (e.g., $K_m$) correlating an average weight of a mammal to an average body surface area can be used to correlate a drug dosage (e.g., a dosage of ADAMTS13), expressed in units of protein (e.g., mass or activity) per body weight of the mammal (e.g., kg), used for a first type of mammal (e.g., a mouse) with a corresponding dose in a second type of mammal (e.g., a human). For review, see Reagan-Shaw et al., FASEB, 22:659-62 (2007). For example, this can be done by first multiplying the drug dosage administered to the first type of mammal by the conversion factor determined for that mammal, and then dividing the product by the conversion factor determined for the second type of mammal. Examples of such conversion factors are given below in Table 1, adopted from the U.S. Department of Health and Human Services guidelines for estimating the maximum safe starting dose in initial clinical trials for therapeutics in adult healthy volunteers.

TABLE 1

Conversion of animal doses to human equivalent doses based on body surface area.

| | To Convert Animal Dose in mg/kg to Dose in | To Convert Animal Dose in mg/kg to HED[a] in mg/kg, Either: | |
|---|---|---|---|
| | mg/m², Multiply by $k_m$ | Divide Animal Dose By | Multiply Animal Dose By |
| Species | | | |
| Human | 37 | — | — |
| Child (20 kg)[b] | 25 | — | — |
| Mouse | 3 | 12.3 | 0.08 |
| Hamster | 5 | 7.4 | 0.13 |
| Rat | 6 | 6.2 | 0.16 |
| Ferret | 7 | 5.3 | 0.19 |
| Guinea pig | 8 | 4.6 | 0.22 |
| Rabbit | 12 | 3.1 | 0.32 |
| Dog | 20 | 1.8 | 0.54 |
| Primates: | | | |
| Monkeys[c] | 12 | 3.1 | 0.32 |
| Marmoset | 6 | 6.2 | 0.16 |
| Squirrel monkey | 7 | 5.3 | 0.19 |
| Baboon | 20 | 1.8 | 0.54 |
| Micro-pig | 27 | 1.4 | 0.73 |
| Mini-pig | 35 | 1.1 | 0.95 |

[a]Assumes 60 kg human. For species not listed or for weights outside the standard ranges. HED can be calculated from the following formula: HED = animal dose in mg/kg × (animal weight in kg/human weight in kg)[0.33].
[b]This $k_m$ value is provided for reference only since healthy children will rarely be volunteers for phase 1 trials.
[c]For example, cynomolgus, rhesus, and stumptail.

In certain embodiments, the bioavailability of the ADAMTS13 after subcutaneous administration is between at least 50% and at least 80% as compared to intravenous administration normalized for the same dose. In certain embodiments, the bioavailability of the ADAMTS13 after subcutaneous administration is between at least 60% and at least 80% as compared to intravenous administration normalized for the same dose. In certain embodiments, the bioavailability of the ADAMTS13 after subcutaneous administration is between at least 50% and 70% as compared to intravenous administration normalized for the same dose. In certain embodiments, the bioavailability of the ADAMTS13 after subcutaneous administration is between at least 55% and 65% as compared to intravenous administration normalized for the same dose. In certain embodiments, the bioavailability of the ADAMTS13 after subcutaneous administration is between at least 55% and 70% as compared to intravenous administration normalized for the same dose.

In certain embodiments, the bioavailability of the ADAMTS13 after subcutaneous administration is at least 40%, or at least 45%, or at least 50%, or at least 51%, or at least 52%, or at least 53%, or at least 54%, or at least 55%, or at least 56%, or at least 57%, or at least 58%, or at least 59%, or at least 60%, or at least 61%, or at least 62%, or at least 63%, or at least 64%, or at least 65%, or at least 66%, or at least 67%, or at least 68%, or at least 69%, or at least 70%, or at least 71%, or at least 72%, or at least 73%, or at least 74%, or at least 75%, or at least 76%, or at least 77%, or at least 78%, or at least 79%, or at least 80%, or at least 81%, or at least 82%, or at least 83%, or at least 84%, or at least 85% as compared to intravenous administration normalized for the same dose.

In certain embodiments, the ADAMTS13 formulation is subcutaneously administered in a single bolus injection. In certain embodiments, the ADAMTS13 formulation is subcutaneously administered monthly. In certain embodiments, the ADAMTS13 formulation is subcutaneously administered every two weeks. In certain embodiments, the ADAMTS13 formulation is subcutaneously administered weekly. In certain embodiments, the ADAMTS13 formulation is subcutaneously administered twice a week. In certain embodiments, the ADAMTS13 formulation is subcutaneously administered daily. In certain embodiments, the ADAMTS13 formulation is subcutaneously administered every 12 hours. In certain embodiments, the ADAMTS13 formulation is subcutaneously administered every 8 hours. In certain embodiments, the ADAMTS13 formulation is subcutaneously administered every six hours. In certain embodiments, the ADAMTS13 formulation is subcutaneously administered every four hours. In certain embodiments, the ADAMTS13 formulation is subcutaneously administered every two hours.

In one embodiment, the ADAMTS13 formulation is subcutaneously administered in a dose and frequency combination selected from variations 1 to 1133 in Table 2. Generally, the dose and frequency of ADAMTS13 administered to a mammal will depend upon, among other factors, the disease or condition being treated, the species of the mammal, the age of the mammal, and the overall health of the mammal.

TABLE 2

Useful combinations of ADAMTS13 dosage and frequency for subcutaneous administration.

| Dose (UFV73/kg body weight) | One Time Monthly | Two Times Monthly | Three Times Monthly | One time Weekly | Two Times Weekly | Every Other Day | One Time Daily | Two Times Daily | Three Times Daily | Four Times Daily | Six Times Daily |
|---|---|---|---|---|---|---|---|---|---|---|---|
| 20-4000 | Var. 1 | Var. 104 | Var. 207 | Var. 310 | Var. 413 | Var. 516 | Var. 619 | Var. 722 | Var. 825 | Var. 928 | Var. 1031 |
| 20-3000 | Var. 2 | Var. 105 | Var. 208 | Var. 311 | Var. 414 | Var. 517 | Var. 620 | Var. 723 | Var. 826 | Var. 929 | Var. 1032 |
| 20-2000 | Var. 3 | Var. 106 | Var. 209 | Var. 312 | Var. 415 | Var. 518 | Var. 621 | Var. 724 | Var. 827 | Var. 930 | Var. 1033 |
| 20-1000 | Var. 4 | Var. 107 | Var. 210 | Var. 313 | Var. 416 | Var. 519 | Var. 622 | Var. 725 | Var. 828 | Var. 931 | Var. 1034 |
| 20-750 | Var. 5 | Var. 108 | Var. 211 | Var. 314 | Var. 417 | Var. 520 | Var. 623 | Var. 726 | Var. 829 | Var. 932 | Var. 1035 |
| 20-500 | Var. 6 | Var. 109 | Var. 212 | Var. 315 | Var. 418 | Var. 521 | Var. 624 | Var. 727 | Var. 830 | Var. 933 | Var. 1036 |
| 20-250 | Var. 7 | Var. 110 | Var. 213 | Var. 316 | Var. 419 | Var. 522 | Var. 625 | Var. 728 | Var. 831 | Var. 934 | Var. 1037 |
| 20-200 | Var. 8 | Var. 111 | Var. 214 | Var. 317 | Var. 420 | Var. 523 | Var. 626 | Var. 729 | Var. 832 | Var. 935 | Var. 1038 |
| 20-150 | Var. 9 | Var. 112 | Var. 215 | Var. 318 | Var. 421 | Var. 524 | Var. 627 | Var. 730 | Var. 833 | Var. 936 | Var. 1039 |
| 20-100 | Var. 10 | Var. 113 | Var. 216 | Var. 319 | Var. 422 | Var. 525 | Var. 628 | Var. 731 | Var. 834 | Var. 937 | Var. 1040 |
| 20-75 | Var. 11 | Var. 114 | Var. 217 | Var. 320 | Var. 423 | Var. 526 | Var. 629 | Var. 732 | Var. 835 | Var. 938 | Var. 1041 |
| 20-50 | Var. 12 | Var. 115 | Var. 218 | Var. 321 | Var. 424 | Var. 527 | Var. 630 | Var. 733 | Var. 836 | Var. 939 | Var. 1042 |
| 20-40 | Var. 13 | Var. 116 | Var. 219 | Var. 322 | Var. 425 | Var. 528 | Var. 631 | Var. 734 | Var. 837 | Var. 940 | Var. 1043 |
| 40-4000 | Var. 14 | Var. 117 | Var. 220 | Var. 323 | Var. 426 | Var. 529 | Var. 632 | Var. 735 | Var. 838 | Var. 941 | Var. 1044 |
| 40-3000 | Var. 15 | Var. 118 | Var. 221 | Var. 324 | Var. 427 | Var. 530 | Var. 633 | Var. 736 | Var. 839 | Var. 942 | Var. 1045 |
| 40-2000 | Var. 16 | Var. 119 | Var. 222 | Var. 325 | Var. 428 | Var. 531 | Var. 634 | Var. 737 | Var. 840 | Var. 943 | Var. 1046 |
| 40-1000 | Var. 17 | Var. 120 | Var. 223 | Var. 326 | Var. 429 | Var. 532 | Var. 635 | Var. 738 | Var. 841 | Var. 944 | Var. 1047 |
| 40-750 | Var. 18 | Var. 121 | Var. 224 | Var. 327 | Var. 430 | Var. 533 | Var. 636 | Var. 739 | Var. 842 | Var. 945 | Var. 1048 |
| 40-500 | Var. 19 | Var. 122 | Var. 225 | Var. 328 | Var. 431 | Var. 534 | Var. 637 | Var. 740 | Var. 843 | Var. 946 | Var. 1049 |
| 40-250 | Var. 20 | Var. 123 | Var. 226 | Var. 329 | Var. 432 | Var. 535 | Var. 638 | Var. 741 | Var. 844 | Var. 947 | Var. 1050 |
| 40-200 | Var. 21 | Var. 124 | Var. 227 | Var. 330 | Var. 433 | Var. 536 | Var. 639 | Var. 742 | Var. 845 | Var. 948 | Var. 1051 |
| 40-150 | Var. 22 | Var. 125 | Var. 228 | Var. 331 | Var. 434 | Var. 537 | Var. 640 | Var. 743 | Var. 846 | Var. 949 | Var. 1052 |
| 40-100 | Var. 23 | Var. 126 | Var. 229 | Var. 332 | Var. 435 | Var. 538 | Var. 641 | Var. 744 | Var. 847 | Var. 950 | Var. 1053 |
| 40-75 | Var. 24 | Var. 127 | Var. 230 | Var. 333 | Var. 436 | Var. 539 | Var. 642 | Var. 745 | Var. 848 | Var. 951 | Var. 1054 |
| 60-4000 | Var. 25 | Var. 128 | Var. 231 | Var. 334 | Var. 437 | Var. 540 | Var. 643 | Var. 746 | Var. 849 | Var. 952 | Var. 1055 |
| 60-3000 | Var. 26 | Var. 129 | Var. 232 | Var. 335 | Var. 438 | Var. 541 | Var. 644 | Var. 747 | Var. 850 | Var. 953 | Var. 1056 |
| 60-2000 | Var. 27 | Var. 130 | Var. 233 | Var. 336 | Var. 439 | Var. 542 | Var. 645 | Var. 748 | Var. 851 | Var. 954 | Var. 1057 |
| 60-1000 | Var. 28 | Var. 131 | Var. 234 | Var. 337 | Var. 440 | Var. 543 | Var. 646 | Var. 749 | Var. 852 | Var. 955 | Var. 1058 |
| 60-750 | Var. 29 | Var. 132 | Var. 235 | Var. 338 | Var. 441 | Var. 544 | Var. 647 | Var. 750 | Var. 853 | Var. 956 | Var. 1059 |
| 60-500 | Var. 30 | Var. 133 | Var. 236 | Var. 339 | Var. 442 | Var. 545 | Var. 648 | Var. 751 | Var. 854 | Var. 957 | Var. 1060 |
| 60-250 | Var. 31 | Var. 134 | Var. 237 | Var. 340 | Var. 443 | Var. 546 | Var. 649 | Var. 752 | Var. 855 | Var. 958 | Var. 1061 |
| 60-200 | Var. 32 | Var. 135 | Var. 238 | Var. 341 | Var. 444 | Var. 547 | Var. 650 | Var. 753 | Var. 856 | Var. 959 | Var. 1062 |

TABLE 2-continued

Useful combinations of ADAMTS13 dosage and frequency for subcutaneous administration.

| Dose (UFV73/kg body weight) | One Time Monthly | Two Times Monthly | Three Times Monthly | One time Weekly | Two Times Weekly | Every Other Day | One Time Daily | Two Times Daily | Three Times Daily | Four Times Daily | Six Times Daily |
|---|---|---|---|---|---|---|---|---|---|---|---|
| 60-150 | Var. 33 | Var. 136 | Var. 239 | Var. 342 | Var. 445 | Var. 548 | Var. 651 | Var. 754 | Var. 857 | Var. 960 | Var. 1063 |
| 60-100 | Var. 34 | Var. 137 | Var. 240 | Var. 343 | Var. 446 | Var. 549 | Var. 652 | Var. 755 | Var. 858 | Var. 961 | Var. 1064 |
| 80-4000 | Var. 35 | Var. 138 | Var. 241 | Var. 344 | Var. 447 | Var. 550 | Var. 653 | Var. 756 | Var. 859 | Var. 962 | Var. 1065 |
| 80-3000 | Var. 36 | Var. 139 | Var. 242 | Var. 345 | Var. 448 | Var. 551 | Var. 654 | Var. 757 | Var. 860 | Var. 963 | Var. 1066 |
| 80-2000 | Var. 37 | Var. 140 | Var. 243 | Var. 346 | Var. 449 | Var. 552 | Var. 655 | Var. 758 | Var. 861 | Var. 964 | Var. 1067 |
| 80-1000 | Var. 38 | Var. 141 | Var. 244 | Var. 347 | Var. 450 | Var. 553 | Var. 656 | Var. 759 | Var. 862 | Var. 965 | Var. 1068 |
| 80-750 | Var. 39 | Var. 142 | Var. 245 | Var. 348 | Var. 451 | Var. 554 | Var. 657 | Var. 760 | Var. 863 | Var. 966 | Var. 1069 |
| 80-500 | Var. 40 | Var. 143 | Var. 246 | Var. 349 | Var. 452 | Var. 555 | Var. 658 | Var. 761 | Var. 864 | Var. 967 | Var. 1070 |
| 80-250 | Var. 41 | Var. 144 | Var. 247 | Var. 350 | Var. 453 | Var. 556 | Var. 659 | Var. 762 | Var. 865 | Var. 968 | Var. 1071 |
| 80-200 | Var. 42 | Var. 145 | Var. 248 | Var. 351 | Var. 454 | Var. 557 | Var. 660 | Var. 763 | Var. 866 | Var. 969 | Var. 1072 |
| 80-150 | Var. 43 | Var. 146 | Var. 249 | Var. 352 | Var. 455 | Var. 558 | Var. 661 | Var. 764 | Var. 867 | Var. 970 | Var. 1073 |
| 80-100 | Var. 44 | Var. 147 | Var. 250 | Var. 353 | Var. 456 | Var. 559 | Var. 662 | Var. 765 | Var. 868 | Var. 971 | Var. 1074 |
| 100-4000 | Var. 45 | Var. 148 | Var. 251 | Var. 354 | Var. 457 | Var. 560 | Var. 663 | Var. 766 | Var. 869 | Var. 972 | Var. 1075 |
| 100-3000 | Var. 46 | Var. 149 | Var. 252 | Var. 355 | Var. 458 | Var. 561 | Var. 664 | Var. 767 | Var. 870 | Var. 973 | Var. 1076 |
| 100-2000 | Var. 47 | Var. 150 | Var. 253 | Var. 356 | Var. 459 | Var. 562 | Var. 665 | Var. 768 | Var. 871 | Var. 974 | Var. 1077 |
| 100-1000 | Var. 48 | Var. 151 | Var. 254 | Var. 357 | Var. 460 | Var. 563 | Var. 666 | Var. 769 | Var. 872 | Var. 975 | Var. 1078 |
| 100-750 | Var. 49 | Var. 152 | Var. 255 | Var. 358 | Var. 461 | Var. 564 | Var. 667 | Var. 770 | Var. 873 | Var. 976 | Var. 1079 |
| 100-500 | Var. 50 | Var. 153 | Var. 256 | Var. 359 | Var. 462 | Var. 565 | Var. 668 | Var. 771 | Var. 874 | Var. 977 | Var. 1080 |
| 100-250 | Var. 51 | Var. 154 | Var. 257 | Var. 360 | Var. 463 | Var. 566 | Var. 669 | Var. 772 | Var. 875 | Var. 978 | Var. 1081 |
| 100-200 | Var. 52 | Var. 155 | Var. 258 | Var. 361 | Var. 464 | Var. 567 | Var. 670 | Var. 773 | Var. 876 | Var. 979 | Var. 1082 |
| 100-150 | Var. 53 | Var. 156 | Var. 259 | Var. 362 | Var. 465 | Var. 568 | Var. 671 | Var. 774 | Var. 877 | Var. 980 | Var. 1083 |
| 200-4000 | Var. 54 | Var. 157 | Var. 260 | Var. 363 | Var. 466 | Var. 569 | Var. 672 | Var. 775 | Var. 878 | Var. 981 | Var. 1084 |
| 200-3000 | Var. 55 | Var. 158 | Var. 261 | Var. 364 | Var. 467 | Var. 570 | Var. 673 | Var. 776 | Var. 879 | Var. 982 | Var. 1085 |
| 200-2000 | Var. 56 | Var. 159 | Var. 262 | Var. 365 | Var. 468 | Var. 571 | Var. 674 | Var. 777 | Var. 880 | Var. 983 | Var. 1086 |
| 200-1000 | Var. 57 | Var. 160 | Var. 263 | Var. 366 | Var. 469 | Var. 572 | Var. 675 | Var. 778 | Var. 881 | Var. 984 | Var. 1087 |
| 200-750 | Var. 58 | Var. 161 | Var. 264 | Var. 367 | Var. 470 | Var. 573 | Var. 676 | Var. 779 | Var. 882 | Var. 985 | Var. 1088 |
| 200-500 | Var. 59 | Var. 162 | Var. 265 | Var. 368 | Var. 471 | Var. 574 | Var. 677 | Var. 780 | Var. 883 | Var. 986 | Var. 1089 |
| 200-250 | Var. 60 | Var. 163 | Var. 266 | Var. 369 | Var. 472 | Var. 575 | Var. 678 | Var. 781 | Var. 884 | Var. 987 | Var. 1090 |
| 400-4000 | Var. 61 | Var. 164 | Var. 267 | Var. 370 | Var. 473 | Var. 576 | Var. 679 | Var. 782 | Var. 885 | Var. 988 | Var. 1091 |
| 400-3000 | Var. 62 | Var. 165 | Var. 268 | Var. 371 | Var. 474 | Var. 577 | Var. 680 | Var. 783 | Var. 886 | Var. 989 | Var. 1092 |
| 400-2000 | Var. 63 | Var. 166 | Var. 269 | Var. 372 | Var. 475 | Var. 578 | Var. 681 | Var. 784 | Var. 887 | Var. 990 | Var. 1093 |
| 400-1000 | Var. 64 | Var. 167 | Var. 270 | Var. 373 | Var. 476 | Var. 579 | Var. 682 | Var. 785 | Var. 888 | Var. 991 | Var. 1094 |
| 400-750 | Var. 65 | Var. 168 | Var. 271 | Var. 374 | Var. 477 | Var. 580 | Var. 683 | Var. 786 | Var. 889 | Var. 992 | Var. 1095 |
| 400-500 | Var. 66 | Var. 169 | Var. 272 | Var. 375 | Var. 478 | Var. 581 | Var. 684 | Var. 787 | Var. 890 | Var. 993 | Var. 1096 |
| 600-4000 | Var. 67 | Var. 170 | Var. 273 | Var. 376 | Var. 479 | Var. 582 | Var. 685 | Var. 788 | Var. 891 | Var. 994 | Var. 1097 |
| 600-3000 | Var. 68 | Var. 171 | Var. 274 | Var. 377 | Var. 480 | Var. 583 | Var. 686 | Var. 789 | Var. 892 | Var. 995 | Var. 1098 |

TABLE 2-continued

Useful combinations of ADAMTS13 dosage and frequency for subcutaneous administration.

| Dose (UFV73/kg body weight) | One Time Monthly | Two Times Monthly | Three Times Monthly | One time Weekly | Two Times Weekly | Every Other Day | One Time Daily | Two Times Daily | Three Times Daily | Four Times Daily | Six Times Daily |
|---|---|---|---|---|---|---|---|---|---|---|---|
| 600-2000 | Var. 69 | Var. 172 | Var. 275 | Var. 378 | Var. 481 | Var. 584 | Var. 687 | Var. 790 | Var. 893 | Var. 996 | Var. 1099 |
| 600-1000 | Var. 70 | Var. 173 | Var. 276 | Var. 379 | Var. 482 | Var. 585 | Var. 688 | Var. 791 | Var. 894 | Var. 997 | Var. 1100 |
| 600-750 | Var. 71 | Var. 174 | Var. 277 | Var. 380 | Var. 483 | Var. 586 | Var. 689 | Var. 792 | Var. 895 | Var. 998 | Var. 1101 |
| 1000-4000 | Var. 72 | Var. 175 | Var. 278 | Var. 381 | Var. 484 | Var. 587 | Var. 690 | Var. 793 | Var. 896 | Var. 999 | Var. 1102 |
| 1000-3000 | Var. 73 | Var. 176 | Var. 279 | Var. 382 | Var. 485 | Var. 588 | Var. 691 | Var. 794 | Var. 897 | Var. 1000 | Var. 1103 |
| 1000-2000 | Var. 74 | Var. 177 | Var. 280 | Var. 383 | Var. 486 | Var. 589 | Var. 692 | Var. 795 | Var. 898 | Var. 1001 | Var. 1104 |
| 2000-4000 | Var. 75 | Var. 178 | Var. 281 | Var. 384 | Var. 487 | Var. 590 | Var. 693 | Var. 796 | Var. 899 | Var. 1002 | Var. 1105 |
| 2000-3000 | Var. 76 | Var. 179 | Var. 282 | Var. 385 | Var. 488 | Var. 591 | Var. 694 | Var. 797 | Var. 900 | Var. 1003 | Var. 1106 |
| 3000-4000 | Var. 77 | Var. 180 | Var. 283 | Var. 386 | Var. 489 | Var. 592 | Var. 695 | Var. 798 | Var. 901 | Var. 1004 | Var. 1107 |
| 20 ± 10% | Var. 78 | Var. 181 | Var. 284 | Var. 387 | Var. 490 | Var. 593 | Var. 696 | Var. 799 | Var. 902 | Var. 1005 | Var. 1108 |
| 40 ± 10% | Var. 79 | Var. 182 | Var. 285 | Var. 388 | Var. 491 | Var. 594 | Var. 697 | Var. 800 | Var. 903 | Var. 1006 | Var. 1109 |
| 60 ± 10% | Var. 80 | Var. 183 | Var. 286 | Var. 389 | Var. 492 | Var. 595 | Var. 698 | Var. 801 | Var. 904 | Var. 1007 | Var. 1110 |
| 80 ± 10% | Var. 81 | Var. 184 | Var. 287 | Var. 390 | Var. 493 | Var. 596 | Var. 699 | Var. 802 | Var. 905 | Var. 1008 | Var. 1111 |
| 100 ± 10% | Var. 82 | Var. 185 | Var. 288 | Var. 391 | Var. 494 | Var. 597 | Var. 700 | Var. 803 | Var. 906 | Var. 1009 | Var. 1112 |
| 150 ± 10% | Var. 83 | Var. 186 | Var. 289 | Var. 392 | Var. 495 | Var. 598 | Var. 701 | Var. 804 | Var. 907 | Var. 1010 | Var. 1113 |
| 200 ± 10% | Var. 84 | Var. 187 | Var. 290 | Var. 393 | Var. 496 | Var. 599 | Var. 702 | Var. 805 | Var. 908 | Var. 1011 | Var. 1114 |
| 250 ± 10% | Var. 85 | Var. 188 | Var. 291 | Var. 394 | Var. 497 | Var. 600 | Var. 703 | Var. 806 | Var. 909 | Var. 1012 | Var. 1115 |
| 300 ± 10% | Var. 86 | Var. 189 | Var. 292 | Var. 395 | Var. 498 | Var. 601 | Var. 704 | Var. 807 | Var. 910 | Var. 1013 | Var. 1116 |
| 350 ± 10% | Var. 87 | Var. 190 | Var. 293 | Var. 396 | Var. 499 | Var. 602 | Var. 705 | Var. 808 | Var. 911 | Var. 1014 | Var. 1117 |
| 400 ± 10% | Var. 88 | Var. 191 | Var. 294 | Var. 397 | Var. 500 | Var. 603 | Var. 706 | Var. 809 | Var. 912 | Var. 1015 | Var. 1118 |
| 450 ± 10% | Var. 89 | Var. 192 | Var. 295 | Var. 398 | Var. 501 | Var. 604 | Var. 707 | Var. 810 | Var. 913 | Var. 1016 | Var. 1119 |
| 500 ± 10% | Var. 90 | Var. 193 | Var. 296 | Var. 399 | Var. 502 | Var. 605 | Var. 708 | Var. 811 | Var. 914 | Var. 1017 | Var. 1120 |
| 600 ± 10% | Var. 91 | Var. 194 | Var. 297 | Var. 400 | Var. 503 | Var. 606 | Var. 709 | Var. 812 | Var. 915 | Var. 1018 | Var. 1121 |
| 700 ± 10% | Var. 92 | Var. 195 | Var. 298 | Var. 401 | Var. 504 | Var. 607 | Var. 710 | Var. 813 | Var. 916 | Var. 1019 | Var. 1122 |
| 800 ± 10% | Var. 93 | Var. 196 | Var. 299 | Var. 402 | Var. 505 | Var. 608 | Var. 711 | Var. 814 | Var. 917 | Var. 1020 | Var. 1123 |
| 900 ± 10% | Var. 94 | Var. 197 | Var. 300 | Var. 403 | Var. 506 | Var. 609 | Var. 712 | Var. 815 | Var. 918 | Var. 1021 | Var. 1124 |
| 1000 ± 10% | Var. 95 | Var. 198 | Var. 301 | Var. 404 | Var. 507 | Var. 610 | Var. 713 | Var. 816 | Var. 919 | Var. 1022 | Var. 1125 |
| 1250 ± 10% | Var. 96 | Var. 199 | Var. 302 | Var. 405 | Var. 508 | Var. 611 | Var. 714 | Var. 817 | Var. 920 | Var. 1023 | Var. 1126 |
| 1500 ± 10% | Var. 97 | Var. 200 | Var. 303 | Var. 406 | Var. 509 | Var. 612 | Var. 715 | Var. 818 | Var. 921 | Var. 1024 | Var. 1127 |
| 1750 ± 10% | Var. 98 | Var. 201 | Var. 304 | Var. 407 | Var. 510 | Var. 613 | Var. 716 | Var. 819 | Var. 922 | Var. 1025 | Var. 1128 |
| 2000 ± 10% | Var. 99 | Var. 202 | Var. 305 | Var. 408 | Var. 511 | Var. 614 | Var. 717 | Var. 820 | Var. 923 | Var. 1026 | Var. 1129 |
| 2500 ± 10% | Var. 100 | Var. 203 | Var. 306 | Var. 409 | Var. 512 | Var. 615 | Var. 718 | Var. 821 | Var. 924 | Var. 1027 | Var. 1130 |
| 3000 ± 10% | Var. 101 | Var. 204 | Var. 307 | Var. 410 | Var. 513 | Var. 616 | Var. 719 | Var. 822 | Var. 925 | Var. 1028 | Var. 1131 |
| 3500 ± 10% | Var. 102 | Var. 205 | Var. 308 | Var. 411 | Var. 514 | Var. 617 | Var. 720 | Var. 823 | Var. 926 | Var. 1029 | Var. 1132 |
| 4000 ± 10% | Var. 103 | Var. 206 | Var. 309 | Var. 412 | Var. 515 | Var. 618 | Var. 721 | Var. 824 | Var. 927 | Var. 1030 | Var. 1133 |

In certain embodiments, about 120-300% of the amount of a standard intravenous dose of an ADAMTS13 formulation for a specific indication as measured in activity units per kilogram is administered subcutaneously. In a specific embodiment, about 120% of the amount of a standard intravenous dose of an ADAMTS13 formulation for a specific indication as measured in activity units per kilogram is administered subcutaneously. In a specific embodiment, about 130% of the amount of a standard intravenous dose of an ADAMTS13 formulation for a specific indication as measured in activity units per kilogram is administered subcutaneously. In a specific embodiment, about 140% of the amount of a standard intravenous dose of an ADAMTS13 formulation for a specific indication as measured in activity units per kilogram is administered subcutaneously. In a specific embodiment, about 150% of the amount of a standard intravenous dose of an ADAMTS13 formulation for a specific indication as measured in activity units per kilogram is administered subcutaneously. In a specific embodiment, about 160% of the amount of a standard intravenous dose of an ADAMTS13 formulation for a specific indication as measured in activity units per kilogram is administered subcutaneously. In a specific embodiment, about 170% of the amount of a standard intravenous dose of an ADAMTS13 formulation for a specific indication as measured in activity units per kilogram is administered subcutaneously. In a specific embodiment, about 180% of the amount of a standard intravenous dose of an ADAMTS13 formulation for a specific indication as measured in activity units per kilogram is administered subcutaneously. In a specific embodiment, about 190% of the amount of a standard intravenous dose of an ADAMTS13 formulation for a specific indication as measured in activity units per kilogram is administered subcutaneously.

In a specific embodiment, about 200% of the amount of a standard intravenous dose of an ADAMTS13 formulation for a specific indication as measured in activity units per kilogram is administered subcutaneously. In a specific embodiment, about 210% of the amount of a standard intravenous dose of an ADAMTS13 formulation for a specific indication as measured in activity units per kilogram is administered subcutaneously. In a specific embodiment, about 220% of the amount of a standard intravenous dose of an ADAMTS13 formulation for a specific indication as measured in activity units per kilogram is administered subcutaneously. In a specific embodiment, about 230% of the amount of a standard intravenous dose of an ADAMTS13 formulation for a specific indication as measured in activity units per kilogram is administered subcutaneously. In a specific embodiment, about 240% of the amount of a standard intravenous dose of an ADAMTS13 formulation for a specific indication as measured in activity units per kilogram is administered subcutaneously. In a specific embodiment, about 250% of the amount of a standard intravenous dose of an ADAMTS13 formulation for a specific indication as measured in activity units per kilogram is administered subcutaneously. In a specific embodiment, about 260% of the amount of a standard intravenous dose of an ADAMTS13 formulation for a specific indication as measured in activity units per kilogram is administered subcutaneously. In a specific embodiment, about 270% of the amount of a standard intravenous dose of an ADAMTS13 formulation for a specific indication as measured in activity units per kilogram is administered subcutaneously. In a specific embodiment, about 280% of the amount of a standard intravenous dose of an ADAMTS13 formulation for a specific indication as measured in activity units per kilogram is administered subcutaneously. In a specific embodiment, about 290% of the amount of a standard intravenous dose of an ADAMTS13 formulation for a specific indication as measured in activity units per kilogram is administered subcutaneously. In a specific embodiment, about 300% of the amount of a standard intravenous dose of an ADAMTS13 formulation for a specific indication as measured in activity units per kilogram is administered subcutaneously.

In certain embodiments, about 120%, about 122%, about 125%, about 127%, about 130%, about 132%, about 135%, about 137%, about 140%, about 142%, about 145%, about 147%, about 150%, about 152%, about 155%, about 157%, about 160%, about 162%, about 165%, about 167%, about 170%, about 172%, about 175%, about 177%, about 180%, about 182%, about 185%, about 187%, about 190%, about 192%, about 195%, about 97%, about 200%, about 202%, about 205%, about 207%, about 210%, about 212%, about 215%, about 217%, about 220%, about 222%, about 225%, about 227%, about 230%, about 232%, about 235%, about 237%, about 240%, about 242%, about 245%, about 247%, about 250%, about 252%, about 255%, about 257%, about 260%, about 262%, about 265%, about 267%, about 270%, about 272%, about 275%, about 277%, about 280%, about 282%, about 285%, about 287%, about 290%, about 292%, about 295%, about 297%, or about 300% of the amount of a standard intravenous dose of an ADAMTS13 formulation for a specific indication as measured in activity units per kilogram is administered subcutaneously.

In one embodiment, an ADAMTS13 formulation is administered subcutaneously to reduce inflammation caused by the clotting disorder (e.g., an infarction), thereby preventing or reducing tissue damage (e.g., damage to the cerebral damage) and/or to reduce reperfusion injury by preventing leukocyte infiltration and damage. In one embodiment, an ADAMTS13 formulation is administered subcutaneously to protect against secondary injury to infarct tissue (e.g., cerebral tissue and myocardial tissue) caused by reperfusion.

Inherited TTP

In one embodiment, an ADAMTS13 formulation described herein is used for the treatment and prophylaxis of inherited TTP. Inherited TTP is due to genetic mutations of the ADAMTS13 gene. Inherited TTP can lead to neurologic manifestations (e.g., mental status, stroke, seizures, hemiplegia, paresthesias, visual disturbance, and aphasia), fatigue, and severe bleeding. If left untreated, acquired TTP can be fatal or can cause lasting physiological damage. Furthermore, because inherited TTP is due to a genetic mutation, life-long treatment is needed and patient compliance is required. While intravenous delivery of ADAMTS13 formulations is effective at treating inherited TTP, intravenous delivery of drugs is not easy for patients to handle (especially children with inherited TTP) and decreases patient compliance. Accordingly, it would be beneficial to develop a subcutaneous ADAMTS13 formulation and a method of ADAMTS13 subcutaneous delivery.

In one embodiment, the disclosure provides a method for treating inherited TTP in a mammal in need thereof, the method including subcutaneously administering a therapeutically effective amount of a composition comprising isolated ADAMTS13 to the mammal, where the therapeutically effective amount of ADAMTS13 is from 20 to 4000 units of FRETS-VWF73 activity per kilogram body weight of the mammal ($U_{FV73}$/kg). In a specific embodiment, the mammal is a human. In one embodiment, the 20 $U_{FV73}$ to 4000 $U_{FV73}$/kg ADAMTS13 is administered about once a month.

In one embodiment, the 20 to 4000 $U_{FV73}$/kg ADAMTS13 is administered about twice a month. In one embodiment, the 20 to 4000 $U_{FV73}$/kg ADAMTS13 is administered about once a week. In one embodiment, the 20 to 4000 $U_{FV73}$/kg ADAMTS13 is administered about twice a week. In one embodiment, the 20 to 4000 $U_{FV73}$/kg ADAMTS13 is administered about once every 48 hours. In one embodiment, the 20 to 4000 $U_{FV73}$/kg ADAMTS13 is administered about once every 24 hours. In one embodiment, the 20 to 4000 $U_{FV73}$/kg ADAMTS13 is administered about once every 12 hours.

In one embodiment, the disclosure provides a method for treating inherited TTP in a mammal in need thereof, the method including subcutaneously administering a therapeutically effective amount of a composition comprising isolated ADAMTS13 to the mammal, where the therapeutically effective amount of ADAMTS13 is from 20 to 2000 units of FRETS-VWF73 activity per kilogram body weight of the mammal ($U_{FV73}$/kg). In a specific embodiment, the mammal is a human. In one embodiment, the 20 $U_{FV73}$ to 2000 $U_{FV73}$/kg ADAMTS13 is administered about once a month. In one embodiment, the 20 to 2000 $U_{FV73}$/kg ADAMTS13 is administered about twice a month. In one embodiment, the 20 to 2000 $U_{FV73}$/kg ADAMTS13 is administered about once a week. In one embodiment, the 20 to 2000 $U_{FV73}$/kg ADAMTS13 is administered about twice a week. In one embodiment, the 20 to 2000 $U_{FV73}$/kg ADAMTS13 is administered about once every 48 hours. In one embodiment, the 20 to 2000 $U_{FV73}$/kg ADAMTS13 is administered about once every 24 hours. In one embodiment, the 20 to 2000 $U_{FV73}$/kg ADAMTS13 is administered about once every 12 hours.

In one embodiment, the disclosure provides a method for treating inherited TTP in a mammal in need thereof, the method including subcutaneously administering a therapeutically effective amount of a composition comprising isolated ADAMTS13 to the mammal, where the therapeutically effective amount of ADAMTS13 is from 20 to 1000 units of FRETS-VWF73 activity per kilogram body weight of the mammal ($U_{FV73}$/kg). In a specific embodiment, the mammal is a human. In one embodiment, the 20 $U_{FV73}$ to 1000 $U_{FV73}$/kg ADAMTS13 is administered about once a month. In one embodiment, the 20 to 1000 $U_{FV73}$/kg ADAMTS13 is administered about twice a month. In one embodiment, the 20 to 1000 $U_{FV73}$/kg ADAMTS13 is administered about once a week. In one embodiment, the 20 to 1000 $U_{FV73}$/kg ADAMTS13 is administered about twice a week. In one embodiment, the 20 to 1000 $U_{FV73}$/kg ADAMTS13 is administered about once every 48 hours. In one embodiment, the 20 to 1000 $U_{FV73}$/kg ADAMTS13 is administered about once every 24 hours. In one embodiment, the 20 to 1000 $U_{FV73}$/kg ADAMTS13 is administered about once every 12 hours.

In one embodiment, the disclosure provides a method for treating inherited TTP in a mammal in need thereof, the method including subcutaneously administering a therapeutically effective amount of a composition comprising isolated ADAMTS13 to the mammal, where the therapeutically effective amount of ADAMTS13 is from 20 to 500 units of FRETS-VWF73 activity per kilogram body weight of the mammal ($U_{FV73}$/kg). In a specific embodiment, the mammal is a human. In one embodiment, the 20 $U_{FV73}$ to 500 $U_{FV73}$/kg ADAMTS13 is administered about once a month. In one embodiment, the 20 to 500 $U_{FV73}$/kg ADAMTS13 is administered about twice a month. In one embodiment, the 20 to 500 $U_{FV73}$/kg ADAMTS13 is administered about once a week. In one embodiment, the 20 to 500 $U_{FV73}$/kg ADAMTS13 is administered about twice a week. In one embodiment, the 20 to 500 $U_{FV73}$/kg ADAMTS13 is administered about once every 48 hours. In one embodiment, the 20 to 500 $U_{FV73}$/kg ADAMTS13 is administered about once every 24 hours. In one embodiment, the 20 to 500 $U_{FV73}$/kg ADAMTS13 is administered about once every 12 hours.

In one embodiment, the disclosure provides a method for treating inherited TTP in a mammal in need thereof, the method including subcutaneously administering a therapeutically effective amount of a composition comprising isolated ADAMTS13 to the mammal, where the therapeutically effective amount of ADAMTS13 is from 20 to 200 units of FRETS-VWF73 activity per kilogram body weight of the mammal ($U_{FV73}$/kg). In a specific embodiment, the mammal is a human. In one embodiment, the 20 $U_{FV73}$ to 200 $U_{FV73}$/kg ADAMTS13 is administered about once a month. In one embodiment, the 20 to 200 $U_{FV73}$/kg ADAMTS13 is administered about twice a month. In one embodiment, the 20 to 200 $U_{FV73}$/kg ADAMTS13 is administered about once a week. In one embodiment, the 20 to 200 $U_{FV73}$/kg ADAMTS13 is administered about twice a week. In one embodiment, the 20 to 200 $U_{FV73}$/kg ADAMTS13 is administered about once every 48 hours. In one embodiment, the 20 to 200 $U_{FV73}$/kg ADAMTS13 is administered about once every 24 hours. In one embodiment, the 20 to 200 $U_{FV73}$/kg ADAMTS13 is administered about once every 12 hours.

In one embodiment, the disclosure provides a method for treating inherited TTP in a mammal in need thereof, the method including subcutaneously administering a therapeutically effective amount of a composition comprising isolated ADAMTS13 to the mammal, where the therapeutically effective amount of ADAMTS13 is from 20 to 100 units of FRETS-VWF73 activity per kilogram body weight of the mammal ($U_{FV73}$/kg). In a specific embodiment, the mammal is a human. In one embodiment, the 20 $U_{FV73}$ to 100 $U_{FV73}$/kg ADAMTS13 is administered about once a month. In one embodiment, the 20 to 100 $U_{FV73}$/kg ADAMTS13 is administered about twice a month. In one embodiment, the 20 to 100 $U_{FV73}$/kg ADAMTS13 is administered about once a week. In one embodiment, the 20 to 100 $U_{FV73}$/kg ADAMTS13 is administered about twice a week. In one embodiment, the 20 to 100 $U_{FV73}$/kg ADAMTS13 is administered about once every 48 hours. In one embodiment, the 20 to 100 $U_{FV73}$/kg ADAMTS13 is administered about once every 24 hours. In one embodiment, the 20 to 100 $U_{FV73}$/kg ADAMTS13 is administered about once every 12 hours.

In one embodiment, the disclosure provides a method for treating inherited TTP in a mammal in need thereof, the method including subcutaneously administering a therapeutically effective amount of a composition comprising isolated ADAMTS13 to the mammal, where the therapeutically effective amount of ADAMTS13 is from 40 to 200 units of FRETS-VWF73 activity per kilogram body weight of the mammal ($U_{FV73}$/kg). In a specific embodiment, the mammal is a human. In one embodiment, the 40 $U_{FV73}$ to 200 $U_{FV73}$/kg ADAMTS13 is administered about once a month. In one embodiment, the 40 to 200 $U_{FV73}$/kg ADAMTS13 is administered about twice a month. In one embodiment, the 40 to 200 $U_{FV73}$/kg ADAMTS13 is administered about once a week. In one embodiment, the 40 to 200 $U_{FV73}$/kg ADAMTS13 is administered about twice a week. In one embodiment, the 40 to 200 $U_{FV73}$/kg ADAMTS13 is administered about once every 48 hours. In one embodiment, the 40 to 200 $U_{FV73}$/kg ADAMTS13 is administered about once every 24 hours. In one embodiment, the 40 to 200 $U_{FV73}$/kg ADAMTS13 is administered about once every 12 hours.

In one embodiment, the disclosure provides a method for treating inherited TTP in a mammal in need thereof, the method including subcutaneously administering a therapeutically effective amount of a composition comprising isolated ADAMTS13 to the mammal, where the therapeutically effective amount of ADAMTS13 and frequency of the dosing is selected from variations 1 to 1133 in Table 2. In a specific embodiment, the mammal is a human.

Acquired TTP

In specific embodiments, an ADAMTS13 formulation described herein is used for the treatment and prophylaxis of acquired TTP. In acquired TTP, patients have a low ADAMTS13 activity due to the development of autoimmune antibodies directed at ADAMTS13. Immune-complexed ADAMTS13 is inactivated, neutralized and/or cleared from the blood stream and patient plasma. Reduced ADAMTS13 activity leads to the accumulation of large uncleaved VWF multimers which can spontaneously adhere to platelets and leading to platelet-VWF-rich thrombi in the microcirculation. Like inherited TTP, acquired TTP can also lead to neurologic manifestations (e.g., mental status, stroke, seizures, hemiplegia, paresthesias, visual disturbance, and aphasia), fatigue, and severe bleeding. If left untreated, acquired TTP can be fatal or can cause lasting physiological damage. Accordingly, patient compliance of ADAMTS13 administration is necessary to prevent permanent damage and eventual fatalities. Thus, it would be beneficial to develop a subcutaneous ADAMTS13 formulation and a method of ADAMTS13 subcutaneous delivery to increase patient ease and compliance as described above.

In one embodiment, the disclosure provides a method for treating acquired TTP in a mammal in need thereof, the method including subcutaneously administering a therapeutically effective amount of a composition comprising isolated ADAMTS13 to the mammal, where the therapeutically effective amount of ADAMTS13 is from 20 to 4000 units of FRETS-VWF73 activity per kilogram body weight of the mammal ($U_{FV73}$/kg). In a specific embodiment, the mammal is a human. In one embodiment, the 20 $U_{FV73}$ to 4000 $U_{FV73}$/kg ADAMTS13 is administered about once a month. In one embodiment, the 20 to 4000 $U_{FV73}$/kg ADAMTS13 is administered about twice a month. In one embodiment, the 20 to 4000 $U_{FV73}$/kg ADAMTS13 is administered about once a week. In one embodiment, the 20 to 4000 $U_{FV73}$/kg ADAMTS13 is administered about twice a week. In one embodiment, the 20 to 4000 $U_{FV73}$/kg ADAMTS13 is administered about once every 48 hours. In one embodiment, the 20 to 4000 $U_{FV73}$/kg ADAMTS13 is administered about once every 24 hours. In one embodiment, the 20 to 4000 $U_{FV73}$/kg ADAMTS13 is administered about once every 12 hours.

In one embodiment, the disclosure provides a method for treating acquired TTP in a mammal in need thereof, the method including subcutaneously administering a therapeutically effective amount of a composition comprising isolated ADAMTS13 to the mammal, where the therapeutically effective amount of ADAMTS13 is from 20 to 2000 units of FRETS-VWF73 activity per kilogram body weight of the mammal ($U_{FV73}$/kg). In a specific embodiment, the mammal is a human. In one embodiment, the 20 $U_{FV73}$ to 2000 $U_{FV73}$/kg ADAMTS13 is administered about once a month. In one embodiment, the 20 to 2000 $U_{FV73}$/kg ADAMTS13 is administered about twice a month. In one embodiment, the 20 to 2000 $U_{FV73}$/kg ADAMTS13 is administered about once a week. In one embodiment, the 20 to 2000 $U_{FV73}$/kg ADAMTS13 is administered about twice a week. In one embodiment, the 20 to 2000 $U_{FV73}$/kg ADAMTS13 is administered about once every 48 hours. In one embodiment, the 20 to 2000 $U_{FV73}$/kg ADAMTS13 is administered about once every 24 hours. In one embodiment, the 20 to 2000 $U_{FV73}$/kg ADAMTS13 is administered about once every 12 hours.

In one embodiment, the disclosure provides a method for treating acquired TTP in a mammal in need thereof, the method including subcutaneously administering a therapeutically effective amount of a composition comprising isolated ADAMTS13 to the mammal, where the therapeutically effective amount of ADAMTS13 is from 20 to 1000 units of FRETS-VWF73 activity per kilogram body weight of the mammal ($U_{FV73}$/kg). In a specific embodiment, the mammal is a human. In one embodiment, the 20 $U_{FV73}$ to 1000 $U_{FV73}$/kg ADAMTS13 is administered about once a month. In one embodiment, the 20 to 1000 $U_{FV73}$/kg ADAMTS13 is administered about twice a month. In one embodiment, the 20 to 1000 $U_{FV73}$/kg ADAMTS13 is administered about once a week. In one embodiment, the 20 to 1000 $U_{FV73}$/kg ADAMTS13 is administered about twice a week. In one embodiment, the 20 to 1000 $U_{FV73}$/kg ADAMTS13 is administered about once every 48 hours. In one embodiment, the 20 to 1000 $U_{FV73}$/kg ADAMTS13 is administered about once every 24 hours. In one embodiment, the 20 to 1000 $U_{FV73}$/kg ADAMTS13 is administered about once every 12 hours.

In one embodiment, the disclosure provides a method for treating acquired TTP in a mammal in need thereof, the method including subcutaneously administering a therapeutically effective amount of a composition comprising isolated ADAMTS13 to the mammal, where the therapeutically effective amount of ADAMTS13 is from 20 to 500 units of FRETS-VWF73 activity per kilogram body weight of the mammal ($U_{FV73}$/kg). In a specific embodiment, the mammal is a human. In one embodiment, the 20 $U_{FV73}$ to 500 $U_{FV73}$/kg ADAMTS13 is administered about once a month. In one embodiment, the 20 to 500 $U_{FV73}$/kg ADAMTS13 is administered about twice a month. In one embodiment, the 20 to 500 $U_{FV73}$/kg ADAMTS13 is administered about once a week. In one embodiment, the 20 to 500 $U_{FV73}$/kg ADAMTS13 is administered about twice a week. In one embodiment, the 20 to 500 $U_{FV73}$/kg ADAMTS13 is administered about once every 48 hours. In one embodiment, the 20 to 500 $U_{FV73}$/kg ADAMTS13 is administered about once every 24 hours. In one embodiment, the 20 to 500 $U_{FV73}$/kg ADAMTS13 is administered about once every 12 hours.

In one embodiment, the disclosure provides a method for treating acquired TTP in a mammal in need thereof, the method including subcutaneously administering a therapeutically effective amount of a composition comprising isolated ADAMTS13 to the mammal, where the therapeutically effective amount of ADAMTS13 is from 20 to 200 units of FRETS-VWF73 activity per kilogram body weight of the mammal ($U_{FV73}$/kg). In a specific embodiment, the mammal is a human. In one embodiment, the 20 $U_{FV73}$ to 200 $U_{FV73}$/kg ADAMTS13 is administered about once a month. In one embodiment, the 20 to 200 $U_{FV73}$/kg ADAMTS13 is administered about twice a month. In one embodiment, the 20 to 200 $U_{FV73}$/kg ADAMTS13 is administered about once a week. In one embodiment, the 20 to 200 $U_{FV73}$/kg ADAMTS13 is administered about twice a week. In one embodiment, the 20 to 200 $U_{FV73}$/kg ADAMTS13 is administered about once every 48 hours. In one embodiment, the 20 to 200 $U_{FV73}$/kg ADAMTS13 is administered about once every 24 hours. In one embodiment, the 20 to 200 $U_{FV73}$/kg ADAMTS13 is administered about once every 12 hours.

In one embodiment, the disclosure provides a method for treating acquired TTP in a mammal in need thereof, the method including subcutaneously administering a therapeutically effective amount of a composition comprising isolated ADAMTS13 to the mammal, where the therapeutically effective amount of ADAMTS13 is from 20 to 100 units of FRETS-VWF73 activity per kilogram body weight of the mammal ($U_{FV73}$/kg). In a specific embodiment, the mammal is a human. In one embodiment, the 20 $U_{FV73}$ to 100 $U_{FV73}$/kg ADAMTS13 is administered about once a month. In one embodiment, the 20 to 100 $U_{FV73}$/kg ADAMTS13 is administered about twice a month. In one embodiment, the 20 to 100 $U_{FV73}$/kg ADAMTS13 is administered about once a week. In one embodiment, the 20 to 100 $U_{FV73}$/kg ADAMTS13 is administered about twice a week. In one embodiment, the 20 to 100 $U_{FV73}$/kg ADAMTS13 is administered about once every 48 hours. In one embodiment, the 20 to 100 $U_{FV73}$/kg ADAMTS13 is administered about once every 24 hours. In one embodiment, the 20 to 100 $U_{FV73}$/kg ADAMTS13 is administered about once every 12 hours.

In one embodiment, the disclosure provides a method for treating acquired TTP in a mammal in need thereof, the method including subcutaneously administering a therapeutically effective amount of a composition comprising isolated ADAMTS13 to the mammal, where the therapeutically effective amount of ADAMTS13 is from 40 to 200 units of FRETS-VWF73 activity per kilogram body weight of the mammal ($U_{FV73}$/kg). In a specific embodiment, the mammal is a human. In one embodiment, the 40 $U_{FV73}$ to 200 $U_{FV73}$/kg ADAMTS13 is administered about once a month. In one embodiment, the 40 to 200 $U_{FV73}$/kg ADAMTS13 is administered about twice a month. In one embodiment, the 40 to 200 $U_{FV73}$/kg ADAMTS13 is administered about once a week. In one embodiment, the 40 to 200 $U_{FV73}$/kg ADAMTS13 is administered about twice a week. In one embodiment, the 40 to 200 $U_{FV73}$/kg ADAMTS13 is administered about once every 48 hours. In one embodiment, the 40 to 200 $U_{FV73}$/kg ADAMTS13 is administered about once every 24 hours. In one embodiment, the 40 to 200 $U_{FV73}$/kg ADAMTS13 is administered about once every 12 hours.

In one embodiment, the disclosure provides a method for treating acquired TTP in a mammal in need thereof, the method including subcutaneously administering a therapeutically effective amount of a composition comprising isolated ADAMTS13 to the mammal, where the therapeutically effective amount of ADAMTS13 and frequency of the dosing is selected from variations 1 to 1133 in Table 2. In a specific embodiment, the mammal is a human.

Myocardial Infarction and Reperfusion Injury

In specific embodiments, an ADAMTS13 formulation described herein is used for the treatment and prophylaxis of myocardial infarction. In specific embodiments, an ADAMTS13 formulation described herein is used for the treatment and prophylaxis of ischemic/reperfusion injury. Reperfusion is the restoration of blood supply to tissue that is ischemic, due to decrease in blood supply. Reperfusion is a procedure for treating infarction (e.g., myocardial infarction and cerebral infarction) or other ischemia, by enabling viable ischemic tissue to recover, thus limiting further necrosis. However, reperfusion can itself further damage the ischemic tissue, causing reperfusion injury. For example, acute myocardial infarction (AMI) is caused by thrombotic occlusion of a coronary artery. In addition to the immediate injury that occurs during deprivation of blood flow, ischemic/reperfusion injury involves tissue injury that occurs after blood flow is restored from the reperfusion.

Furthermore, it has been reported that ADAMTS13 has an anti-inflammatory effect that prevents or decreases secondary injury during ischemic reperfusion. De Meyer et al. ("Protective anti-inflammatory effect of ADAMTS13 on myocardial ischemia/reperfusion injury in mice," Blood, 2012, 120(26):5217-5223). As described by De Meyer et al., VWF and ADAMTS13 are involved in platelet adhesion and thrombus formation because ADAMTS13 cleaves the most thrombogenic VWF multimers into smaller and less hemostatically active VWF fragments. De Meyer et al. also describe ADAMTS's role in down-regulating inflammatory responses. It has also been shown that ADAMTS13 can reduce thrombosis and inflammation (e.g., atherosclerosis). Chauhan et al. ("ADAMTS13: a new link between thrombosis and inflammation," J Exp Med., 2008, 205:2065-2074); Chauhan et al. ("Systemic antithrombotic effects of ADAMTS13," J Exp Med., 2006, 203:767-776; Gandhi et al. ("ADAMTS13 reduces vascular inflammation and the development of early atherosclerosis in mice," Blood, 2012, 119(10):2385-2391.

De Meyer et al. suggest that ADAMTS13 prevents excessive VWF-mediated platelet and leukocyte recruitment in the ischemic myocardium by cleaving VWF. Based on this hypothesis, De Meyer et al. show that neutrophil infiltration in the myocardium of animals with induced myocardial infarction was nine times lower when the animals were treated ADAMTS13. Accordingly, De Meyer et al. show that ADAMTS13 reduces inflammatory responses in ischemic myocardium. This reduced inflammation also reduces reperfusion injury by preventing leukocyte infiltration and damage. Thus, it would be beneficial to subcutaneously administer an ADAMTS13 formulation to patients to avoid inflammation that results in tissue damage during infarction (e.g., myocardial infarction and cerebral infarction) and reperfusion because subcutaneous administration is easier and faster to administer than intravenous compositions that are generally administered by a medical professional.

In some embodiments, the pharmaceutical composition is administered immediately upon discovery of a myocardial infarction, e.g., within 5 minutes, 10 minutes, 15 minutes, 20 minutes, 25 minutes, 30 minutes, 35 minutes, 40 minutes, 45 minutes, 50 minutes, 55 minutes, 60 minutes, 90 minutes, 110 minutes, 120 minutes, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 or more hours, or any combination thereof, for treatment of the infarction and/or reperfusion injury. Accordingly, it is important to have a pharmaceutical composition that can be quickly and easily administered.

In one embodiment, the disclosure provides a method for treating myocardial infarction in a mammal in need thereof, the method including subcutaneously administering a therapeutically effective amount of a composition comprising isolated ADAMTS13 to the mammal, where the therapeutically effective amount of ADAMTS13 is from 20 to 4000 units of FRETS-VWF73 activity per kilogram body weight of the mammal ($U_{FV73}$/kg). In a specific embodiment, the mammal is a human. In one embodiment, the 20 $U_{FV73}$ to 4000 $U_{FV73}$/kg ADAMTS13 is administered within 10 minutes of discovery of a myocardial infarction in the mammal. In one embodiment, the 20 to 4000 $U_{FV73}$/kg ADAMTS13 is administered within 30 minutes of discovery of a myocardial infarction in the mammal. In one embodiment, the 20 to 4000 $U_{FV73}$/kg ADAMTS13 is administered within 60 minutes of discovery of a myocardial infarction in the mammal. In one embodiment, the 20 to 4000 $U_{FV73}$/kg ADAMTS13 is administered within 4 hours of discovery of a myocardial infarction in the mammal. In one embodiment, the 20 to 4000 $U_{FV73}$/kg ADAMTS13 is administered within 12 hours of discovery of a myocardial infarction in the mammal. In one embodiment, the 20 to 4000 $U_{FV73}$/kg ADAMTS13 is administered within 24 hours of discovery of a myocardial infarction in the mammal.

In one embodiment, the disclosure provides a method for treating myocardial infarction in a mammal in need thereof, the method including subcutaneously administering a therapeutically effective amount of a composition comprising isolated ADAMTS13 to the mammal, where the therapeutically effective amount of ADAMTS13 is from 20 to 2000 units of FRETS-VWF73 activity per kilogram body weight of the mammal ($U_{FV73}$/kg). In a specific embodiment, the mammal is a human. In one embodiment, the 20 $U_{FV73}$ to 2000 $U_{FV73}$/kg ADAMTS13 is administered within 10 minutes of discovery of a myocardial infarction in the mammal. In one embodiment, the 20 to 2000 $U_{FV73}$/kg ADAMTS13 is administered within 30 minutes of discovery of a myocardial infarction in the mammal. In one embodiment, the 20 to 2000 $U_{FV73}$/kg ADAMTS13 is administered within 60 minutes of discovery of a myocardial infarction in the mammal. In one embodiment, the 20 to 2000 $U_{FV73}$/kg ADAMTS13 is administered within 4 hours of discovery of a myocardial infarction in the mammal. In one embodiment, the 20 to 2000 $U_{FV73}$/kg ADAMTS13 is administered within 12 hours of discovery of a myocardial infarction in the mammal. In one embodiment, the 20 to 2000 $U_{FV73}$/kg ADAMTS13 is administered within 24 hours of discovery of a myocardial infarction in the mammal.

In one embodiment, the disclosure provides a method for treating myocardial infarction in a mammal in need thereof, the method including subcutaneously administering a therapeutically effective amount of a composition comprising isolated ADAMTS13 to the mammal, where the therapeutically effective amount of ADAMTS13 is from 20 to 1000 units of FRETS-VWF73 activity per kilogram body weight of the mammal ($U_{FV73}$/kg). In a specific embodiment, the mammal is a human. In one embodiment, the 20 $U_{FV73}$ to 1000 $U_{FV73}$/kg ADAMTS13 is administered within 10 minutes of discovery of a myocardial infarction in the mammal. In one embodiment, the 20 to 1000 $U_{FV73}$/kg ADAMTS13 is administered within 30 minutes of discovery of a myocardial infarction in the mammal. In one embodiment, the 20 to 1000 $U_{FV73}$/kg ADAMTS13 is administered within 60 minutes of discovery of a myocardial infarction in the mammal. In one embodiment, the 20 to 1000 $U_{FV73}$/kg ADAMTS13 is administered within 4 hours of discovery of a myocardial infarction in the mammal. In one embodiment, the 20 to 1000 $U_{FV73}$/kg ADAMTS13 is administered within 12 hours of discovery of a myocardial infarction in the mammal. In one embodiment, the 20 to 1000 $U_{FV73}$/kg ADAMTS13 is administered within 24 hours of discovery of a myocardial infarction in the mammal.

In one embodiment, the disclosure provides a method for treating myocardial infarction in a mammal in need thereof, the method including subcutaneously administering a therapeutically effective amount of a composition comprising isolated ADAMTS13 to the mammal, where the therapeutically effective amount of ADAMTS13 is from 20 to 500 units of FRETS-VWF73 activity per kilogram body weight of the mammal ($U_{FV73}$/kg). In a specific embodiment, the mammal is a human. In one embodiment, the 20 $U_{FV73}$ to 500 $U_{FV73}$/kg ADAMTS13 is administered within 10 minutes of discovery of a myocardial infarction in the mammal. In one embodiment, the 20 to 500 $U_{FV73}$/kg ADAMTS13 is administered within 30 minutes of discovery of a myocardial infarction in the mammal. In one embodiment, the 20 to 500 $U_{FV73}$/kg ADAMTS13 is administered within 60 minutes of discovery of a myocardial infarction in the mammal. In one embodiment, the 20 to 500 $U_{FV73}$/kg ADAMTS13 is administered within 4 hours of discovery of a myocardial infarction in the mammal. In one embodiment, the 20 to 500 $U_{FV73}$/kg ADAMTS13 is administered within 12 hours of discovery of a myocardial infarction in the mammal. In one embodiment, the 20 to 500 $U_{FV73}$/kg ADAMTS13 is administered within 24 hours of discovery of a myocardial infarction in the mammal.

In one embodiment, the disclosure provides a method for treating myocardial infarction in a mammal in need thereof, the method including subcutaneously administering a therapeutically effective amount of a composition comprising isolated ADAMTS13 to the mammal, where the therapeutically effective amount of ADAMTS13 is from 20 to 200 units of FRETS-VWF73 activity per kilogram body weight of the mammal ($U_{FV73}$/kg). In a specific embodiment, the mammal is a human. In one embodiment, the 20 $U_{FV73}$ to 200 $U_{FV73}$/kg ADAMTS13 is administered within 10 minutes of discovery of a myocardial infarction in the mammal. In one embodiment, the 20 to 200 $U_{FV73}$/kg ADAMTS13 is administered within 30 minutes of discovery of a myocardial infarction in the mammal. In one embodiment, the 20 to 200 $U_{FV73}$/kg ADAMTS13 is administered within 60 minutes of discovery of a myocardial infarction in the mammal. In one embodiment, the 20 to 200 $U_{FV73}$/kg ADAMTS13 is administered within 4 hours of discovery of a myocardial infarction in the mammal. In one embodiment, the 20 to 200 $U_{FV73}$/kg ADAMTS13 is administered within 12 hours of discovery of a myocardial infarction in the mammal. In one embodiment, the 20 to 200 $U_{FV73}$/kg ADAMTS13 is administered within 24 hours of discovery of a myocardial infarction in the mammal.

In one embodiment, the disclosure provides a method for treating myocardial infarction in a mammal in need thereof, the method including subcutaneously administering a therapeutically effective amount of a composition comprising isolated ADAMTS13 to the mammal, where the therapeutically effective amount of ADAMTS13 is from 20 to 100 units of FRETS-VWF73 activity per kilogram body weight of the mammal ($U_{FV73}$/kg). In a specific embodiment, the mammal is a human. In one embodiment, the 20 $U_{FV73}$ to 100 $U_{FV73}$/kg ADAMTS13 is administered within 10 minutes of discovery of a myocardial infarction in the mammal. In one embodiment, the 20 to 100 $U_{FV73}$/kg ADAMTS13 is administered within 30 minutes of discovery of a myocardial infarction in the mammal. In one embodiment, the 20 to 100 $U_{FV73}$/kg ADAMTS13 is administered within 60 minutes of discovery of a myocardial infarction in the mammal. In one embodiment, the 20 to 100 $U_{FV73}$/kg ADAMTS13 is administered within 4 hours of discovery of a myocardial infarction in the mammal. In one embodiment, the 20 to 100 $U_{FV73}$/kg ADAMTS13 is administered within 12 hours of discovery of a myocardial infarction in the mammal. In one embodiment, the 20 to 100 $U_{FV73}$/kg ADAMTS13 is administered within 24 hours of discovery of a myocardial infarction in the mammal.

In one embodiment, the disclosure provides a method for treating myocardial infarction in a mammal in need thereof, the method including subcutaneously administering a therapeutically effective amount of a composition comprising isolated ADAMTS13 to the mammal, where the therapeutically effective amount of ADAMTS13 is from 40 to 200 units of FRETS-VWF73 activity per kilogram body weight of the mammal ($U_{FV73}$/kg). In a specific embodiment, the mammal is a human. In one embodiment, the 40 $U_{FV73}$ to 200 $U_{FV73}$/kg ADAMTS13 is administered within 10 minutes of discovery of a myocardial infarction in the mammal. In one embodiment, the 40 to 200 $U_{FV73}$/kg ADAMTS13 is administered within 30 minutes of discovery of a myocardial infarction in the mammal. In one embodiment, the 40 to 200 $U_{FV73}$/kg ADAMTS13 is administered within 60 minutes of discovery of a myocardial infarction in the mammal. In one embodiment, the 40 to 200 $U_{FV73}$/kg ADAMTS13 is administered within 4 hours of discovery of a myocardial infarction in the mammal. In one embodiment, the 40 to 200 $U_{FV73}$/kg ADAMTS13 is administered within 12 hours of discovery of a myocardial infarction in the mammal. In one embodiment, the 40 to 200 $U_{FV73}$/kg ADAMTS13 is administered within 24 hours of discovery of a myocardial infarction in the mammal.

Cerebral Infarction

In one embodiment, an ADAMTS13 formulation described herein is used for the treatment and/or prophylaxis of cerebral infarction. Cerebral infarction, commonly referred to as a stroke, occurs when blood flow to part of the brain is prevented. Cerebral infarctions can occur, for example, when a blood vessel that supplies blood to the brain is blocked by a blood clot. A Cerebral infarction can also be the result of a blunt force trauma and mechanical injury. This can either be caused by a clot in an artery of the brain (thrombotic stroke) or by a clot from another part of the body that travels to the brain (embolic stroke). Accordingly, in some embodiments, the invention provides a method of improving the recovery of (or reducing the damage to) sensory and/or motor function in a patient after a cerebral infarction, comprising the step of administering to the individual a pharmaceutical composition comprising a therapeutically effective amount of an ADAMTS13 protein or a biologically active derivative thereof, thereby improving the recovery of (or reducing the damage to) sensory and/or motor function in the individual post-cerebral infarction.

In some embodiments, the pharmaceutical composition is administered immediately upon discovery of a cerebral infarction, e.g., within 5 minutes, 10 minutes, 15 minutes, 20 minutes, 25 minutes, 30 minutes, 35 minutes, 40 minutes, 45 minutes, 50 minutes, 55 minutes, 60 minutes, 90 minutes, 110 minutes, 120 minutes, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 or more hours, or any combination thereof. Accordingly, it is important to have a pharmaceutical composition that can be quickly and easily administered.

In one embodiment, the disclosure provides a method for treating cerebral infarction in a mammal in need thereof, the method including subcutaneously administering a therapeutically effective amount of a composition comprising isolated ADAMTS13 to the mammal, where the therapeutically effective amount of ADAMTS13 is from 20 to 4000 units of FRETS-VWF73 activity per kilogram body weight of the mammal ($U_{FV73}$/kg). In a specific embodiment, the mammal is a human. In one embodiment, the 20 $U_{FV73}$ to 4000 $U_{FV73}$/kg ADAMTS13 is administered within 10 minutes of discovery of a cerebral infarction in the mammal. In one embodiment, the 20 to 4000 $U_{FV73}$/kg ADAMTS13 is administered within 30 minutes of discovery of a cerebral infarction in the mammal. In one embodiment, the 20 to 4000 $U_{FV73}$/kg ADAMTS13 is administered within 60 minutes of discovery of a cerebral infarction in the mammal. In one embodiment, the 20 to 4000 $U_{FV73}$/kg ADAMTS13 is administered within 4 hours of discovery of a cerebral infarction in the mammal. In one embodiment, the 20 to 4000 $U_{FV73}$/kg ADAMTS13 is administered within 12 hours of discovery of a cerebral infarction in the mammal. In one embodiment, the 20 to 4000 $U_{FV73}$/kg ADAMTS13 is administered within 24 hours of discovery of a cerebral infarction in the mammal.

In one embodiment, the disclosure provides a method for treating cerebral infarction in a mammal in need thereof, the method including subcutaneously administering a therapeutically effective amount of a composition comprising isolated ADAMTS13 to the mammal, where the therapeutically effective amount of ADAMTS13 is from 20 to 2000 units of FRETS-VWF73 activity per kilogram body weight of the mammal ($U_{FV73}$/kg). In a specific embodiment, the mammal is a human. In one embodiment, the 20 $U_{FV73}$ to 2000 $U_{FV73}$/kg ADAMTS13 is administered within 10 minutes of discovery of a cerebral infarction in the mammal. In one embodiment, the 20 to 2000 $U_{FV73}$/kg ADAMTS13 is administered within 30 minutes of discovery of a cerebral infarction in the mammal. In one embodiment, the 20 to 2000 $U_{FV73}$/kg ADAMTS13 is administered within 60 minutes of discovery of a cerebral infarction in the mammal. In one embodiment, the 20 to 2000 $U_{FV73}$/kg ADAMTS13 is administered within 4 hours of discovery of a cerebral infarction in the mammal. In one embodiment, the 20 to 2000 $U_{FV73}$/kg ADAMTS13 is administered within 12 hours of discovery of a cerebral infarction in the mammal. In one embodiment, the 20 to 2000 $U_{FV73}$/kg ADAMTS13 is administered within 24 hours of discovery of a cerebral infarction in the mammal.

In one embodiment, the disclosure provides a method for treating cerebral infarction in a mammal in need thereof, the method including subcutaneously administering a therapeutically effective amount of a composition comprising isolated ADAMTS13 to the mammal, where the therapeutically effective amount of ADAMTS13 is from 20 to 1000 units of FRETS-VWF73 activity per kilogram body weight of the mammal ($U_{FV73}$/kg). In a specific embodiment, the mammal is a human. In one embodiment, the 20 $U_{FV73}$ to 1000 $U_{FV73}$/kg ADAMTS13 is administered within 10 minutes of discovery of a cerebral infarction in the mammal. In one embodiment, the 20 to 1000 $U_{FV73}$/kg ADAMTS13 is administered within 30 minutes of discovery of a cerebral infarction in the mammal. In one embodiment, the 20 to 1000 $U_{FV73}$/kg ADAMTS13 is administered within 60 minutes of discovery of a cerebral infarction in the mammal. In one embodiment, the 20 to 1000 $U_{FV73}$/kg ADAMTS13 is administered within 4 hours of discovery of a cerebral infarction in the mammal. In one embodiment, the 20 to 1000 $U_{FV73}$/kg ADAMTS13 is administered within 12 hours of discovery of a cerebral infarction in the mammal. In one embodiment, the 20 to 1000 $U_{FV73}$/kg ADAMTS13 is administered within 24 hours of discovery of a cerebral infarction in the mammal.

In one embodiment, the disclosure provides a method for treating cerebral infarction in a mammal in need thereof, the method including subcutaneously administering a therapeutically effective amount of a composition comprising isolated ADAMTS13 to the mammal, where the therapeutically effective amount of ADAMTS13 is from 20 to 500 units of FRETS-VWF73 activity per kilogram body weight of the mammal ($U_{FV73}$/kg). In a specific embodiment, the mammal is a human. In one embodiment, the 20 $U_{FV73}$ to 500 $U_{FV73}$/kg ADAMTS13 is administered within 10 minutes of discovery of a cerebral infarction in the mammal. In one embodiment, the 20 to 500 $U_{FV73}$/kg ADAMTS13 is administered within 30 minutes of discovery of a cerebral infarction in the mammal. In one embodiment, the 20 to 500 $U_{FV73}$/kg ADAMTS13 is administered within 60 minutes of discovery of a cerebral infarction in the mammal. In one embodiment, the 20 to 500 $U_{FV73}$/kg ADAMTS13 is administered within 4 hours of discovery of a cerebral infarction in the mammal. In one embodiment, the 20 to 500 $U_{FV73}$/kg ADAMTS13 is administered within 12 hours of discovery of a cerebral infarction in the mammal. In one embodiment, the 20 to 500 $U_{FV73}$/kg ADAMTS13 is administered within 24 hours of discovery of a cerebral infarction in the mammal.

In one embodiment, the disclosure provides a method for treating cerebral infarction in a mammal in need thereof, the method including subcutaneously administering a therapeutically effective amount of a composition comprising isolated ADAMTS13 to the mammal, where the therapeutically effective amount of ADAMTS13 is from 20 to 200 units of FRETS-VWF73 activity per kilogram body weight of the mammal ($U_{FV73}$/kg). In a specific embodiment, the mammal is a human. In one embodiment, the 20 $U_{FV73}$ to 200 $U_{FV73}$/kg ADAMTS13 is administered within 10 minutes of discovery of a cerebral infarction in the mammal. In one embodiment, the 20 to 200 $U_{FV73}$/kg ADAMTS13 is administered within 30 minutes of discovery of a cerebral infarction in the mammal. In one embodiment, the 20 to 200 $U_{FV73}$/kg ADAMTS13 is administered within 60 minutes of discovery of a cerebral infarction in the mammal. In one embodiment, the 20 to 200 $U_{FV73}$/kg ADAMTS13 is administered within 4 hours of discovery of a cerebral infarction in the mammal. In one embodiment, the 20 to 200 $U_{FV73}$/kg ADAMTS13 is administered within 12 hours of discovery of a cerebral infarction in the mammal. In one embodiment, the 20 to 200 $U_{FV73}$/kg ADAMTS13 is administered within 24 hours of discovery of a cerebral infarction in the mammal.

In one embodiment, the disclosure provides a method for treating cerebral infarction in a mammal in need thereof, the method including subcutaneously administering a therapeutically effective amount of a composition comprising isolated ADAMTS13 to the mammal, where the therapeutically effective amount of ADAMTS13 is from 20 to 100 units of FRETS-VWF73 activity per kilogram body weight of the mammal ($U_{FV73}$/kg). In a specific embodiment, the mammal is a human. In one embodiment, the 20 $U_{FV73}$ to 100 $U_{FV73}$/kg ADAMTS13 is administered within 10 minutes of discovery of a cerebral infarction in the mammal. In one embodiment, the 20 to 100 $U_{FV73}$/kg ADAMTS13 is administered within 30 minutes of discovery of a cerebral infarction in the mammal. In one embodiment, the 20 to 100 $U_{FV73}$/kg ADAMTS13 is administered within 60 minutes of discovery of a cerebral infarction in the mammal. In one embodiment, the 20 to 100 $U_{FV73}$/kg ADAMTS13 is administered within 4 hours of discovery of a cerebral infarction in the mammal. In one embodiment, the 20 to 100 $U_{FV73}$/kg ADAMTS13 is administered within 12 hours of discovery of a cerebral infarction in the mammal. In one embodiment, the 20 to 100 $U_{FV73}$/kg ADAMTS13 is administered within 24 hours of discovery of a cerebral infarction in the mammal.

In one embodiment, the disclosure provides a method for treating cerebral infarction in a mammal in need thereof, the method including subcutaneously administering a therapeutically effective amount of a composition comprising isolated ADAMTS13 to the mammal, where the therapeutically effective amount of ADAMTS13 is from 40 to 200 units of FRETS-VWF73 activity per kilogram body weight of the mammal ($U_{FV73}$/kg). In a specific embodiment, the mammal is a human. In one embodiment, the 40 $U_{FV73}$ to 200 $U_{FV73}$/kg ADAMTS13 is administered within 10 minutes of discovery of a cerebral infarction in the mammal. In one embodiment, the 40 to 200 $U_{FV73}$/kg ADAMTS13 is administered within 30 minutes of discovery of a cerebral infarction in the mammal. In one embodiment, the 40 to 200 $U_{FV73}$/kg ADAMTS13 is administered within 60 minutes of discovery of a cerebral infarction in the mammal. In one embodiment, the 40 to 200 $U_{FV73}$/kg ADAMTS13 is administered within 4 hours of discovery of a cerebral infarction in the mammal. In one embodiment, the 40 to 200 $U_{FV73}$/kg ADAMTS13 is administered within 12 hours of discovery of a cerebral infarction in the mammal. In one embodiment, the 40 to 200 $U_{FV73}$/kg ADAMTS13 is administered within 24 hours of discovery of a cerebral infarction in the mammal.

Deep Vein Thrombosis

In one embodiment, an ADAMTS13 formulation described herein is used for the treatment and/or prophylaxis of deep vein thrombosis (DVT). DVT is a blood clot that forms in a vein, deep in the body. While most deep vein clots occur in the lower leg or thigh, they can occur throughout the body. DVT is a particularly dangerous disease because a blood clot can break off and travel through the bloodstream (an embolus) to the heart, lungs, or brain, for example. Such embolisms can cause damage to organs and may result in death. Accordingly, as described above, ADAMTS13 formulations can be used to treat DVT and resulting embolisms. Furthermore, because DVT can develop and cause damage quickly, it is important to have a pharmaceutical composition that can be quickly and easily administered. Thus, it would be beneficial to develop a subcutaneous ADAMTS13 formulation and a method of ADAMTS13 subcutaneous delivery.

In some embodiments, an ADAMTS13 pharmaceutical composition is administered immediately upon discovery of a deep vein thrombosis, e.g., within 5 minutes, 10 minutes, 15 minutes, 20 minutes, 25 minutes, 30 minutes, 35 minutes, 40 minutes, 45 minutes, 50 minutes, 55 minutes, 60 minutes, 90 minutes, 110 minutes, 120 minutes, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 or more hours, or any combination thereof. Accordingly, it is important to have a pharmaceutical composition that can be quickly and easily administered.

In one embodiment, the disclosure provides a method for treating deep vein thrombosis in a mammal in need thereof, the method including subcutaneously administering a therapeutically effective amount of a composition comprising isolated ADAMTS13 to the mammal, where the therapeutically effective amount of ADAMTS13 is from 20 to 4000 units of FRETS-VWF73 activity per kilogram body weight of the mammal ($U_{FV73}$/kg). In a specific embodiment, the mammal is a human. In one embodiment, the 20 $U_{FV73}$ to 4000 $U_{FV73}$/kg ADAMTS13 is administered within 10 minutes of discovery of a deep vein thrombosis in the mammal. In one embodiment, the 20 to 4000 $U_{FV73}$/kg ADAMTS13 is administered within 30 minutes of discovery of a deep vein thrombosis in the mammal. In one embodiment, the 20 to 4000 $U_{FV73}$/kg ADAMTS13 is administered within 60 minutes of discovery of a deep vein thrombosis in the mammal. In one embodiment, the 20 to 4000 $U_{FV73}$/kg ADAMTS13 is administered within 4 hours of discovery of a deep vein thrombosis in the mammal. In one embodiment, the 20 to 4000 $U_{FV73}$/kg ADAMTS13 is administered within 12 hours of discovery of a deep vein thrombosis in the mammal. In one embodiment, the 20 to 4000 $U_{FV73}$/kg ADAMTS13 is administered within 24 hours of discovery of a deep vein thrombosis in the mammal.

In one embodiment, the disclosure provides a method for treating deep vein thrombosis in a mammal in need thereof, the method including subcutaneously administering a therapeutically effective amount of a composition comprising isolated ADAMTS13 to the mammal, where the therapeutically effective amount of ADAMTS13 is from 20 to 2000 units of FRETS-VWF73 activity per kilogram body weight of the mammal ($U_{FV73}$/kg). In a specific embodiment, the mammal is a human. In one embodiment, the 20 $U_{FV73}$ to 2000 $U_{FV73}$/kg ADAMTS13 is administered within 10 minutes of discovery of a deep vein thrombosis in the mammal. In one embodiment, the 20 to 2000 $U_{FV73}$/kg ADAMTS13 is administered within 30 minutes of discovery of a deep vein thrombosis in the mammal. In one embodiment, the 20 to 2000 $U_{FV73}$/kg ADAMTS13 is administered within 60 minutes of discovery of a deep vein thrombosis in the mammal. In one embodiment, the 20 to 2000 $U_{FV73}$/kg ADAMTS13 is administered within 4 hours of discovery of a deep vein thrombosis in the mammal. In one embodiment, the 20 to 2000 $U_{FV73}$/kg ADAMTS13 is administered within 12 hours of discovery of a deep vein thrombosis in the mammal. In one embodiment, the 20 to 2000 $U_{FV73}$/kg ADAMTS13 is administered within 24 hours of discovery of a deep vein thrombosis in the mammal.

In one embodiment, the disclosure provides a method for treating deep vein thrombosis in a mammal in need thereof, the method including subcutaneously administering a therapeutically effective amount of a composition comprising isolated ADAMTS13 to the mammal, where the therapeutically effective amount of ADAMTS13 is from 20 to 1000 units of FRETS-VWF73 activity per kilogram body weight of the mammal ($U_{FV73}$/kg). In a specific embodiment, the mammal is a human. In one embodiment, the 20 $U_{FV73}$ to 1000 $U_{FV73}$/kg ADAMTS13 is administered within 10 minutes of discovery of a deep vein thrombosis in the mammal. In one embodiment, the 20 to 1000 $U_{FV73}$/kg ADAMTS13 is administered within 30 minutes of discovery of a deep vein thrombosis in the mammal. In one embodiment, the 20 to 1000 $U_{FV73}$/kg ADAMTS13 is administered within 60 minutes of discovery of a deep vein thrombosis in the mammal. In one embodiment, the 20 to 1000 $U_{FV73}$/kg ADAMTS13 is administered within 4 hours of discovery of a deep vein thrombosis in the mammal. In one embodiment, the 20 to 1000 $U_{FV73}$/kg ADAMTS13 is administered within 12 hours of discovery of a deep vein thrombosis in the mammal. In one embodiment, the 20 to 1000 $U_{FV73}$/kg ADAMTS13 is administered within 24 hours of discovery of a deep vein thrombosis in the mammal.

In one embodiment, the disclosure provides a method for treating deep vein thrombosis in a mammal in need thereof, the method including subcutaneously administering a therapeutically effective amount of a composition comprising isolated ADAMTS13 to the mammal, where the therapeutically effective amount of ADAMTS13 is from 20 to 500 units of FRETS-VWF73 activity per kilogram body weight of the mammal ($U_{FV73}$/kg). In a specific embodiment, the mammal is a human. In one embodiment, the 20 $U_{FV73}$ to 500 $U_{FV73}$/kg ADAMTS13 is administered within 10 minutes of discovery of a deep vein thrombosis in the mammal. In one embodiment, the 20 to 500 $U_{FV73}$/kg ADAMTS13 is administered within 30 minutes of discovery of a deep vein thrombosis in the mammal. In one embodiment, the 20 to 500 $U_{FV73}$/kg ADAMTS13 is administered within 60 minutes of discovery of a deep vein thrombosis in the mammal. In one embodiment, the 20 to 500 $U_{FV73}$/kg ADAMTS13 is administered within 4 hours of discovery of a deep vein thrombosis in the mammal. In one embodiment, the 20 to 500 $U_{FV73}$/kg ADAMTS13 is administered within 12 hours of discovery of a deep vein thrombosis in the mammal. In one embodiment, the 20 to 500 $U_{FV73}$/kg ADAMTS13 is administered within 24 hours of discovery of a deep vein thrombosis in the mammal.

In one embodiment, the disclosure provides a method for treating deep vein thrombosis in a mammal in need thereof, the method including subcutaneously administering a therapeutically effective amount of a composition comprising isolated ADAMTS13 to the mammal, where the therapeutically effective amount of ADAMTS13 is from 20 to 200 units of FRETS-VWF73 activity per kilogram body weight of the mammal ($U_{FV73}$/kg). In a specific embodiment, the mammal is a human. In one embodiment, the 20 $U_{FV73}$ to 200 $U_{FV73}$/kg ADAMTS13 is administered within 10 minutes of discovery of a deep vein thrombosis in the mammal. In one embodiment, the 20 to 200 $U_{FV73}$/kg ADAMTS13 is administered within 30 minutes of discovery of a deep vein thrombosis in the mammal. In one embodiment, the 20 to 200 $U_{FV73}$/kg ADAMTS13 is administered within 60 minutes of discovery of a deep vein thrombosis in the mammal. In one embodiment, the 20 to 200 $U_{FV73}$/kg ADAMTS13 is administered within 4 hours of discovery of a deep vein thrombosis in the mammal. In one embodiment, the 20 to 200 $U_{FV73}$/kg ADAMTS13 is administered within 12 hours of discovery of a deep vein thrombosis in the mammal. In one embodiment, the 20 to 200 $U_{FV73}$/kg ADAMTS13 is administered within 24 hours of discovery of a deep vein thrombosis in the mammal.

In one embodiment, the disclosure provides a method for treating deep vein thrombosis in a mammal in need thereof, the method including subcutaneously administering a therapeutically effective amount of a composition comprising isolated ADAMTS13 to the mammal, where the therapeutically effective amount of ADAMTS13 is from 20 to 100 units of FRETS-VWF73 activity per kilogram body weight of the mammal ($U_{FV73}$/kg). In a specific embodiment, the mammal is a human. In one embodiment, the 20 $U_{FV73}$ to 100 $U_{FV73}$/kg ADAMTS13 is administered within 10 minutes of discovery of a deep vein thrombosis in the mammal. In one embodiment, the 20 to 100 $U_{FV73}$/kg ADAMTS13 is administered within 30 minutes of discovery of a deep vein thrombosis in the mammal. In one embodiment, the 20 to 100 $U_{FV73}$/kg ADAMTS13 is administered within 60 minutes of discovery of a deep vein thrombosis in the mammal. In one embodiment, the 20 to 100 $U_{FV73}$/kg ADAMTS13 is administered within 4 hours of discovery of a deep vein thrombosis in the mammal. In one embodiment, the 20 to 100 $U_{FV73}$/kg ADAMTS13 is administered within 12 hours of discovery of a deep vein thrombosis in the mammal. In one embodiment, the 20 to 100 $U_{FV73}$/kg ADAMTS13 is administered within 24 hours of discovery of a deep vein thrombosis in the mammal.

In one embodiment, the disclosure provides a method for treating deep vein thrombosis in a mammal in need thereof, the method including subcutaneously administering a therapeutically effective amount of a composition comprising isolated ADAMTS13 to the mammal, where the therapeutically effective amount of ADAMTS13 is from 40 to 200 units of FRETS-VWF73 activity per kilogram body weight of the mammal ($U_{FV73}$/kg). In a specific embodiment, the mammal is a human. In one embodiment, the 40 $U_{FV73}$ to 200 $U_{FV73}$/kg ADAMTS13 is administered within 10 minutes of discovery of a deep vein thrombosis in the mammal. In one embodiment, the 40 to 200 $U_{FV73}$/kg ADAMTS13 is administered within 30 minutes of discovery of a deep vein thrombosis in the mammal. In one embodiment, the 40 to 200 U$_{FV73}$/kg ADAMTS13 is administered within 60 minutes of discovery of a deep vein thrombosis in the mammal. In one embodiment, the 40 to 200 U$_{FV73}$/kg ADAMTS13 is administered within 4 hours of discovery of a deep vein thrombosis in the mammal. In one embodiment, the 40 to 200 U$_{FV73}$/kg ADAMTS13 is administered within 12 hours of discovery of a deep vein thrombosis in the mammal. In one embodiment, the 40 to 200 U$_{FV73}$/kg ADAMTS13 is administered within 24 hours of discovery of a deep vein thrombosis in the mammal.

In one embodiment, the disclosure provides a method for prophylactic treatment of a mammal at risk for developing deep vein thrombosis, the method including subcutaneously administering a therapeutically effective amount of a composition comprising isolated ADAMTS13 to the mammal in need therein, where the therapeutically effective amount of ADAMTS13 is from 20 to 4000 units of FRETS-VWF73 activity per kilogram body weight of the mammal (UFV73/kg). In a specific embodiment, the mammal is a human. In one embodiment, the 20 UFV73 to 4000 UFV73/kg ADAMTS13 is administered about once a month. In one embodiment, the 20 to 4000 UFV73/kg ADAMTS13 is administered about twice a month. In one embodiment, the 20 to 4000 UFV73/kg ADAMTS13 is administered about once a week. In one embodiment, the 20 to 4000 UFV73/kg ADAMTS13 is administered about twice a week. In one embodiment, the 20 to 4000 UFV73/kg ADAMTS13 is administered about once every 48 hours. In one embodiment, the 20 to 4000 UFV73/kg ADAMTS13 is administered about once every 24 hours. In one embodiment, the 20 to 4000 UFV73/kg ADAMTS13 is administered about once every 12 hours.

In one embodiment, the disclosure provides a method for prophylactic treatment of a mammal at risk for developing deep vein thrombosis, the method including subcutaneously administering a therapeutically effective amount of a composition comprising isolated ADAMTS13 to the mammal, where the therapeutically effective amount of ADAMTS13 is from 20 to 2000 units of FRETS-VWF73 activity per kilogram body weight of the mammal (UFV73/kg). In a specific embodiment, the mammal is a human. In one embodiment, the 20 UFV73 to 2000 UFV73/kg ADAMTS13 is administered about once a month. In one embodiment, the 20 to 2000 UFV73/kg ADAMTS13 is administered about twice a month. In one embodiment, the 20 to 2000 UFV73/kg ADAMTS13 is administered about once a week. In one embodiment, the 20 to 2000 UFV73/kg ADAMTS13 is administered about twice a week. In one embodiment, the 20 to 2000 UFV73/kg ADAMTS13 is administered about once every 48 hours. In one embodiment, the 20 to 2000 UFV73/kg ADAMTS13 is administered about once every 24 hours. In one embodiment, the 20 to 2000 UFV73/kg ADAMTS13 is administered about once every 12 hours.

In one embodiment, the disclosure provides a method for prophylactic treatment of a mammal at risk for developing deep vein thrombosis, the method including subcutaneously administering a therapeutically effective amount of a composition comprising isolated ADAMTS13 to the mammal, where the therapeutically effective amount of ADAMTS13 is from 20 to 1000 units of FRETS-VWF73 activity per kilogram body weight of the mammal (UFV73/kg). In a specific embodiment, the mammal is a human. In one embodiment, the 20 UFV73 to 1000 UFV73/kg ADAMTS13 is administered about once a month. In one embodiment, the 20 to 1000 UFV73/kg ADAMTS13 is administered about twice a month. In one embodiment, the 20 to 1000 UFV73/kg ADAMTS13 is administered about once a week. In one embodiment, the 20 to 1000 UFV73/kg ADAMTS13 is administered about twice a week. In one embodiment, the 20 to 1000 UFV73/kg ADAMTS13 is administered about once every 48 hours. In one embodiment, the 20 to 1000 UFV73/kg ADAMTS13 is administered about once every 24 hours. In one embodiment, the 20 to 1000 UFV73/kg ADAMTS13 is administered about once every 12 hours.

In one embodiment, the disclosure provides a method for prophylactic treatment of a mammal at risk for developing deep vein thrombosis, the method including subcutaneously administering a therapeutically effective amount of a composition comprising isolated ADAMTS13 to the mammal, where the therapeutically effective amount of ADAMTS13 is from 20 to 500 units of FRETS-VWF73 activity per kilogram body weight of the mammal (UFV73/kg). In a specific embodiment, the mammal is a human. In one embodiment, the 20 UFV73 to 500 UFV73/kg ADAMTS13 is administered about once a month. In one embodiment, the 20 to 500 UFV73/kg ADAMTS13 is administered about twice a month. In one embodiment, the 20 to 500 UFV73/kg ADAMTS13 is administered about once a week. In one embodiment, the 20 to 500 UFV73/kg ADAMTS13 is administered about twice a week. In one embodiment, the 20 to 500 UFV73/kg ADAMTS13 is administered about once every 48 hours. In one embodiment, the 20 to 500 UFV73/kg ADAMTS13 is administered about once every 24 hours. In one embodiment, the 20 to 500 UFV73/kg ADAMTS13 is administered about once every 12 hours.

In one embodiment, the disclosure provides a method for prophylactic treatment of a mammal at risk for developing deep vein thrombosis, the method including subcutaneously administering a therapeutically effective amount of a composition comprising isolated ADAMTS13 to the mammal, where the therapeutically effective amount of ADAMTS13 is from 20 to 200 units of FRETS-VWF73 activity per kilogram body weight of the mammal (UFV73/kg). In a specific embodiment, the mammal is a human. In one embodiment, the 20 UFV73 to 200 UFV73/kg ADAMTS13 is administered about once a month. In one embodiment, the 20 to 200 UFV73/kg ADAMTS13 is administered about twice a month. In one embodiment, the 20 to 200 UFV73/kg ADAMTS13 is administered about once a week. In one embodiment, the 20 to 200 UFV73/kg ADAMTS13 is administered about twice a week. In one embodiment, the 20 to 200 UFV73/kg ADAMTS13 is administered about once every 48 hours. In one embodiment, the 20 to 200 UFV73/kg ADAMTS13 is administered about once every 24 hours. In one embodiment, the 20 to 200 UFV73/kg ADAMTS13 is administered about once every 12 hours.

In one embodiment, the disclosure provides a method for prophylactic treatment of a mammal at risk for developing deep vein thrombosis, the method including subcutaneously administering a therapeutically effective amount of a composition comprising isolated ADAMTS13 to the mammal, where the therapeutically effective amount of ADAMTS13 is from 20 to 100 units of FRETS-VWF73 activity per kilogram body weight of the mammal (UFV73/kg). In a specific embodiment, the mammal is a human. In one embodiment, the 20 UFV73 to 100 UFV73/kg ADAMTS13 is administered about once a month. In one embodiment, the 20 to 100 UFV73/kg ADAMTS13 is administered about twice a month. In one embodiment, the 20 to 100 UFV73/kg ADAMTS13 is administered about once a week. In one embodiment, the 20 to 100 UFV73/kg ADAMTS13 is administered about twice a week. In one embodiment, the 20 to 100 UFV73/kg ADAMTS13 is administered about once every 48 hours. In one embodiment, the 20 to 100 UFV73/kg ADAMTS13 is administered about once every 24 hours. In one embodiment, the 20 to 100 UFV73/kg ADAMTS13 is administered about once every 12 hours.

In one embodiment, the disclosure provides a method for prophylactic treatment of a mammal at risk for developing deep vein thrombosis, the method including subcutaneously administering a therapeutically effective amount of a composition comprising isolated ADAMTS13 to the mammal, where the therapeutically effective amount of ADAMTS13 is from 40 to 200 units of FRETS-VWF73 activity per kilogram body weight of the mammal (UFV73/kg). In a specific embodiment, the mammal is a human. In one embodiment, the 40 UFV73 to 200 UFV73/kg ADAMTS13 is administered about once a month. In one embodiment, the 40 to 200 UFV73/kg ADAMTS13 is administered about twice a month. In one embodiment, the 40 to 200 UFV73/kg ADAMTS13 is administered about once a week. In one embodiment, the 40 to 200 UFV73/kg ADAMTS13 is administered about twice a week. In one embodiment, the 40 to 200 UFV73/kg ADAMTS13 is administered about once every 48 hours. In one embodiment, the 40 to 200 UFV73/kg ADAMTS13 is administered about once every 24 hours. In one embodiment, the 40 to 200 UFV73/kg ADAMTS13 is administered about once every 12 hours.

In one embodiment, the disclosure provides a method for prophylactic treatment of a mammal at risk for developing deep vein thrombosis, the method including subcutaneously administering a therapeutically effective amount of a composition comprising isolated ADAMTS13 to the mammal, where the therapeutically effective amount of ADAMTS13 and frequency of the dosing is selected from variations 1 to 1133 in Table 2. In a specific embodiment, the mammal is a human.

Disseminated Intravascular Coagulation

In specific embodiments, an ADAMTS13 formulation described herein is used for the treatment and prophylaxis of disseminated intravascular coagulation (DIC), specifically, sepsis-related DIC. DIC is a condition in which blood clots form throughout the body's small blood vessels. These blood clots can reduce or block blood flow throughout the body and can result in damage to tissues and organs. The blood clots in the small blood vessels results from an increase in clotting activity. This increase in activity over uses available platelets and clotting factors, thereby also increasing the chance of serious internal and external bleeding by depleting the available source of platelets and clotting factors. Accordingly, a patient with DIC will often suffer from blood clots and severe bleeding disorders.

Certain diseases such as sepsis, surgery/trauma, cancer, complications of childbirth/pregnancy, venomous snake bites (rattlesnakes and vipers), frostbite, and burns can cause clotting factors to become overactive and can lead to DIC. DIC can also be acute (developing quickly over hours or days) or chronic (developing over weeks or months). While both types of DIC require medical treatment, acute DIC must be treated immediately to prevent excessive blood clotting in the small blood vessels that quickly lead to severe bleeding. Accordingly, it is important to have a pharmaceutical composition that can be quickly and easily administered to treat DIC, especially acute DIC such as sepsis-related DIC. Thus, it would be beneficial to develop a subcutaneous ADAMTS13 formulation and a method of ADAMTS13 subcutaneous delivery.

In some embodiments, the pharmaceutical composition is administered immediately upon discovery of disseminated intravascular coagulation, e.g., within 5 minutes, 10 minutes, 15 minutes, 20 minutes, 25 minutes, 30 minutes, 35 minutes, 40 minutes, 45 minutes, 50 minutes, 55 minutes, 60 minutes, 90 minutes, 110 minutes, 120 minutes, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 or more hours, or any combination thereof. Accordingly, it is important to have a pharmaceutical composition that can be quickly and easily administered.

In one embodiment, the disclosure provides a method for treating disseminated intravascular coagulation in a mammal in need thereof, the method including subcutaneously administering a therapeutically effective amount of a composition comprising isolated ADAMTS13 to the mammal, where the therapeutically effective amount of ADAMTS13 is from 20 to 4000 units of FRETS-VWF73 activity per kilogram body weight of the mammal ($U_{FV73}$/kg). In a specific embodiment, the mammal is a human. In one embodiment, the 20 $U_{FV73}$ to 4000 $U_{FV73}$/kg ADAMTS13 is administered within 10 minutes of discovery of disseminated intravascular coagulation in the mammal. In one embodiment, the 20 to 4000 $U_{FV73}$/kg ADAMTS13 is administered within 30 minutes of discovery of disseminated intravascular coagulation in the mammal. In one embodiment, the 20 to 4000 $U_{FV73}$/kg ADAMTS13 is administered within 60 minutes of discovery of disseminated intravascular coagulation in the mammal. In one embodiment, the 20 to 4000 $U_{FV73}$/kg ADAMTS13 is administered within 4 hours of discovery of disseminated intravascular coagulation in the mammal. In one embodiment, the 20 to 4000 $U_{FV73}$/kg ADAMTS13 is administered within 12 hours of discovery of disseminated intravascular coagulation in the mammal. In one embodiment, the 20 to 4000 $U_{FV73}$/kg ADAMTS13 is administered within 24 hours of discovery of disseminated intravascular coagulation in the mammal.

In one embodiment, the disclosure provides a method for treating disseminated intravascular coagulation in a mammal in need thereof, the method including subcutaneously administering a therapeutically effective amount of a composition comprising isolated ADAMTS13 to the mammal, where the therapeutically effective amount of ADAMTS13 is from 20 to 2000 units of FRETS-VWF73 activity per kilogram body weight of the mammal ($U_{FV73}$/kg). In a specific embodiment, the mammal is a human. In one embodiment, the 20 $U_{FV73}$ to 2000 $U_{FV73}$/kg ADAMTS13 is administered within 10 minutes of discovery of disseminated intravascular coagulation in the mammal. In one embodiment, the 20 to 2000 $U_{FV73}$/kg ADAMTS13 is administered within 30 minutes of discovery of disseminated intravascular coagulation in the mammal. In one embodiment, the 20 to 2000 $U_{FV73}$/kg ADAMTS13 is administered within 60 minutes of discovery of disseminated intravascular coagulation in the mammal. In one embodiment, the 20 to 2000 $U_{FV73}$/kg ADAMTS13 is administered within 4 hours of discovery of disseminated intravascular coagulation in the mammal. In one embodiment, the 20 to 2000 $U_{FV73}$/kg ADAMTS13 is administered within 12 hours of discovery of disseminated intravascular coagulation in the mammal. In one embodiment, the 20 to 2000 $U_{FV73}$/kg ADAMTS13 is administered within 24 hours of discovery of disseminated intravascular coagulation in the mammal.

In one embodiment, the disclosure provides a method for treating disseminated intravascular coagulation in a mammal in need thereof, the method including subcutaneously administering a therapeutically effective amount of a composition comprising isolated ADAMTS13 to the mammal, where the therapeutically effective amount of ADAMTS13 is from 20 to 1000 units of FRETS-VWF73 activity per kilogram body weight of the mammal ($U_{FV73}$/kg). In a specific embodiment, the mammal is a human. In one embodiment, the 20 $U_{FV73}$ to 1000 $U_{FV73}$/kg ADAMTS13 is administered within 10 minutes of discovery of disseminated intravascular coagulation in the mammal. In one embodiment, the 20 to 1000 $U_{FV73}$/kg ADAMTS13 is administered within 30 minutes of discovery of disseminated intravascular coagulation in the mammal. In one embodiment, the 20 to 1000 $U_{FV73}$/kg ADAMTS13 is administered within 60 minutes of discovery of disseminated intravascular coagulation in the mammal. In one embodiment, the 20 to 1000 $U_{FV73}$/kg ADAMTS13 is administered within 4 hours of discovery of disseminated intravascular coagulation in the mammal. In one embodiment, the 20 to 1000 $U_{FV73}$/kg ADAMTS13 is administered within 12 hours of discovery of disseminated intravascular coagulation in the mammal. In one embodiment, the 20 to 1000 $U_{FV73}$/kg ADAMTS13 is administered within 24 hours of discovery of disseminated intravascular coagulation in the mammal.

In one embodiment, the disclosure provides a method for treating disseminated intravascular coagulation in a mammal in need thereof, the method including subcutaneously administering a therapeutically effective amount of a composition comprising isolated ADAMTS13 to the mammal, where the therapeutically effective amount of ADAMTS13 is from 20 to 500 units of FRETS-VWF73 activity per kilogram body weight of the mammal ($U_{FV73}$/kg). In a specific embodiment, the mammal is a human. In one embodiment, the 20 $U_{FV73}$ to 500 $U_{FV73}$/kg ADAMTS13 is administered within 10 minutes of discovery of disseminated intravascular coagulation in the mammal. In one embodiment, the 20 to 500 $U_{FV73}$/kg ADAMTS13 is administered within 30 minutes of discovery of disseminated intravascular coagulation in the mammal. In one embodiment, the 20 to 500 $U_{FV73}$/kg ADAMTS13 is administered within 60 minutes of discovery of disseminated intravascular coagulation in the mammal. In one embodiment, the 20 to 500 $U_{FV73}$/kg ADAMTS13 is administered within 4 hours of discovery of disseminated intravascular coagulation in the mammal. In one embodiment, the 20 to 500 $U_{FV73}$/kg ADAMTS13 is administered within 12 hours of discovery of disseminated intravascular coagulation in the mammal. In one embodiment, the 20 to 500 $U_{FV73}$/kg ADAMTS13 is administered within 24 hours of discovery of disseminated intravascular coagulation in the mammal.

In one embodiment, the disclosure provides a method for treating disseminated intravascular coagulation in a mammal in need thereof, the method including subcutaneously administering a therapeutically effective amount of a composition comprising isolated ADAMTS13 to the mammal, where the therapeutically effective amount of ADAMTS13 is from 20 to 200 units of FRETS-VWF73 activity per kilogram body weight of the mammal ($U_{FV73}$/kg). In a specific embodiment, the mammal is a human. In one embodiment, the 20 $U_{FV73}$ to 200 $U_{FV73}$/kg ADAMTS13 is administered within 10 minutes of discovery of disseminated intravascular coagulation in the mammal. In one embodiment, the 20 to 200 $U_{FV73}$/kg ADAMTS13 is administered within 30 minutes of discovery of disseminated intravascular coagulation in the mammal. In one embodiment, the 20 to 200 $U_{FV73}$/kg ADAMTS13 is administered within 60 minutes of discovery of disseminated intravascular coagulation in the mammal. In one embodiment, the 20 to 200 $U_{FV73}$/kg ADAMTS13 is administered within 4 hours of discovery of disseminated intravascular coagulation in the mammal. In one embodiment, the 20 to 200 $U_{FV73}$/kg ADAMTS13 is administered within 12 hours of discovery of disseminated intravascular coagulation in the mammal. In one embodiment, the 20 to 200 $U_{FV73}$/kg ADAMTS13 is administered within 24 hours of discovery of disseminated intravascular coagulation in the mammal.

In one embodiment, the disclosure provides a method for treating disseminated intravascular coagulation in a mammal in need thereof, the method including subcutaneously administering a therapeutically effective amount of a composition comprising isolated ADAMTS13 to the mammal, where the therapeutically effective amount of ADAMTS13 is from 20 to 100 units of FRETS-VWF73 activity per kilogram body weight of the mammal ($U_{FV73}$/kg). In a specific embodiment, the mammal is a human. In one embodiment, the 20 $U_{FV73}$ to 100 $U_{FV73}$/kg ADAMTS13 is administered within 10 minutes of discovery of disseminated intravascular coagulation in the mammal. In one embodiment, the 20 to 100 $U_{FV73}$/kg ADAMTS13 is administered within 30 minutes of discovery of disseminated intravascular coagulation in the mammal. In one embodiment, the 20 to 100 $U_{FV73}$/kg ADAMTS13 is administered within 60 minutes of discovery of disseminated intravascular coagulation in the mammal. In one embodiment, the 20 to 100 $U_{FV73}$/kg ADAMTS13 is administered within 4 hours of discovery of disseminated intravascular coagulation in the mammal. In one embodiment, the 20 to 100 $U_{FV73}$/kg ADAMTS13 is administered within 12 hours of discovery of disseminated intravascular coagulation in the mammal. In one embodiment, the 20 to 100 $U_{FV73}$/kg ADAMTS13 is administered within 24 hours of discovery of disseminated intravascular coagulation in the mammal.

In one embodiment, the disclosure provides a method for treating disseminated intravascular coagulation in a mammal in need thereof, the method including subcutaneously administering a therapeutically effective amount of a composition comprising isolated ADAMTS13 to the mammal, where the therapeutically effective amount of ADAMTS13 is from 40 to 200 units of FRETS-VWF73 activity per kilogram body weight of the mammal ($U_{FV73}$/kg). In a specific embodiment, the mammal is a human. In one embodiment, the 40 $U_{FV73}$ to 200 $U_{FV73}$/kg ADAMTS13 is administered within 10 minutes of discovery of disseminated intravascular coagulation in the mammal. In one embodiment, the 40 to 200 $U_{FV73}$/kg ADAMTS13 is administered within 30 minutes of discovery of disseminated intravascular coagulation in the mammal. In one embodiment, the 40 to 200 $U_{FV73}$/kg ADAMTS13 is administered within 60 minutes of discovery of disseminated intravascular coagulation in the mammal. In one embodiment, the 40 to 200 $U_{FV73}$/kg ADAMTS13 is administered within 4 hours of discovery of disseminated intravascular coagulation in the mammal. In one embodiment, the 40 to 200 $U_{FV73}$/kg ADAMTS13 is administered within 12 hours of discovery of disseminated intravascular coagulation in the mammal. In one embodiment, the 40 to 200 $U_{FV73}$/kg ADAMTS13 is administered within 24 hours of discovery of disseminated intravascular coagulation in the mammal.

V. ADAMTS13 Kits

In another aspect, kits are provided for the treatment of a disease or condition associated with ADAMTS13 or VWF dysfunction. In one embodiment, the kit comprises a formulation of rADAMTS13. In some embodiments, the kits provided herein may contain one or more dose of a liquid or lyophilized formulation as provided herein. When the kits comprise a lyophilized rADAMTS13 formulation, generally the kits will also contain a suitable liquid for reconstitution of the liquid formulation, for example, sterile water or a pharmaceutically acceptable buffer. In some embodiments, a kit includes an ADAMTS13 formulation prepackaged in a syringe for subcutaneous administration by a health care professional or for home use.

In one embodiment, a kit is provided comprising between about 10 units of FRETS-VWF73 activity and about 10,000 units of FRETS-VWF73 activity. In other embodiments, the kit may provide, for example, between about 20 units of FRETS-VWF73 ($U_{FV73}$) activity and about 8,000 units of FRETS-VWF73 activity, or between about 30 $U_{FV73}$ and about 6,000 $U_{FV73}$, or between about 40 $U_{FV73}$ and about 4,000 $U_{FV73}$, or between about 50 $U_{FV73}$ and about 3,000 $U_{FV73}$, or between about 75 $U_{FV73}$ and about 2,500 $U_{FV73}$, or between about 100 $U_{FV73}$ and about 2,000 $U_{FV73}$, or between about 200 $U_{FV73}$ and about 1,500 $U_{FV73}$, or between about other ranges therein. In certain embodiments, a kit may provide about 10 units of FRETS-VWF73 activity, or about 20, 30, 40, 50, 60, 70, 80, 90, 100, 150, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000, 11,000, 12,000, 13,000, 14,000, 15,000, 16,000, 17,000, 18,000, 19,000, 20,000 or more units of FRETS-VWF73 activity.

In certain embodiments, the kit is for a single administration or dose of ADAMTS13. In other embodiments, the kit may contain multiple doses of ADAMTS13 for subcutaneous administration. In one embodiment, the kit may comprise an ADAMTS13 formulation prepackaged in a syringe for subcutaneous administration by a health care professional or for home use.

VI. Examples

Example 1: The Pharmacokinetic Properties of rADAMTS13 with Intravenous and Subcutaneous Administration This study was conducted to evaluate the pharmacokinetic properties of recombinant ADAMTS13 in Göttingen minipigs after intravenous (i.v.) or subcutaneous (s.c.) administration. In this study, 4 male Göttingen minipigs were administered i.v. ADAMTS13 (the "intravenous group") and 4 male Göttingen minipigs were administered s.c. ADAMTS13 (the "subcutaneous group").

Male Göttingen minipigs were trained before the start of the study to cooperate with the study procedures. Thus, the animals were not restrained during administration of anesthetics or the test item and blood sampling.

The animals were anesthetized for catheter implantation using a Zoletil mix consisting of 1.11 mg/kg tiletamine, 1.11 mg/kg zolazepam, 0.56 mg/kg xylazine, 0.56 mg/kg ketamine, and 0.11 mg/kg butorphanole (i.m.). Isoflurane was used for anesthesia maintenance when necessary. The animals received pure oxygen via a mask or an endotracheal tube during surgery. The jugular region was shaved and disinfected. A central catheter was inserted into the cranial V. cava using the Seldinger technique. 4 mg/kg carprofene was administered for analgesia before recovery from anesthesia.

The intravenous group received a nominal dose of 200 FRETS-U/kg rADAMTS13 i.v. (0.085 mL/kg). The subcutaneous group received a nominal dose of 1000 FRETS-U/kg rADAMTS13 s.c. (0.456 mL/kg). Blood was sampled via the central venous catheter before administration of the test item and 5 min, 1 h, 3 h, 6 h, 9 h. 24 h, 32 h, 48 h, 56 h and 72 h after administration of the test item. Blood samples were prepared as follows: the first 0.5-0.7 mL were discarded to avoid dilution with the catheter lock solution (saline). Then, 0.8 mL blood was collected and mixed with 0.2 mL sodium citrate. The blood sample was centrifuged with 5700 rpm (lx 10 min, lx 5 min). The plasma was stored at $<-60°$ C.

ADAMTS13 activity was determined by a FRETS assay and antigen by an ELISA. Furthermore, the potential development of binding antibodies against human rADAMTS13 and the influence of rADAMTS13 on the multimer pattern of endogenous VWF were assessed.

Figure 2:
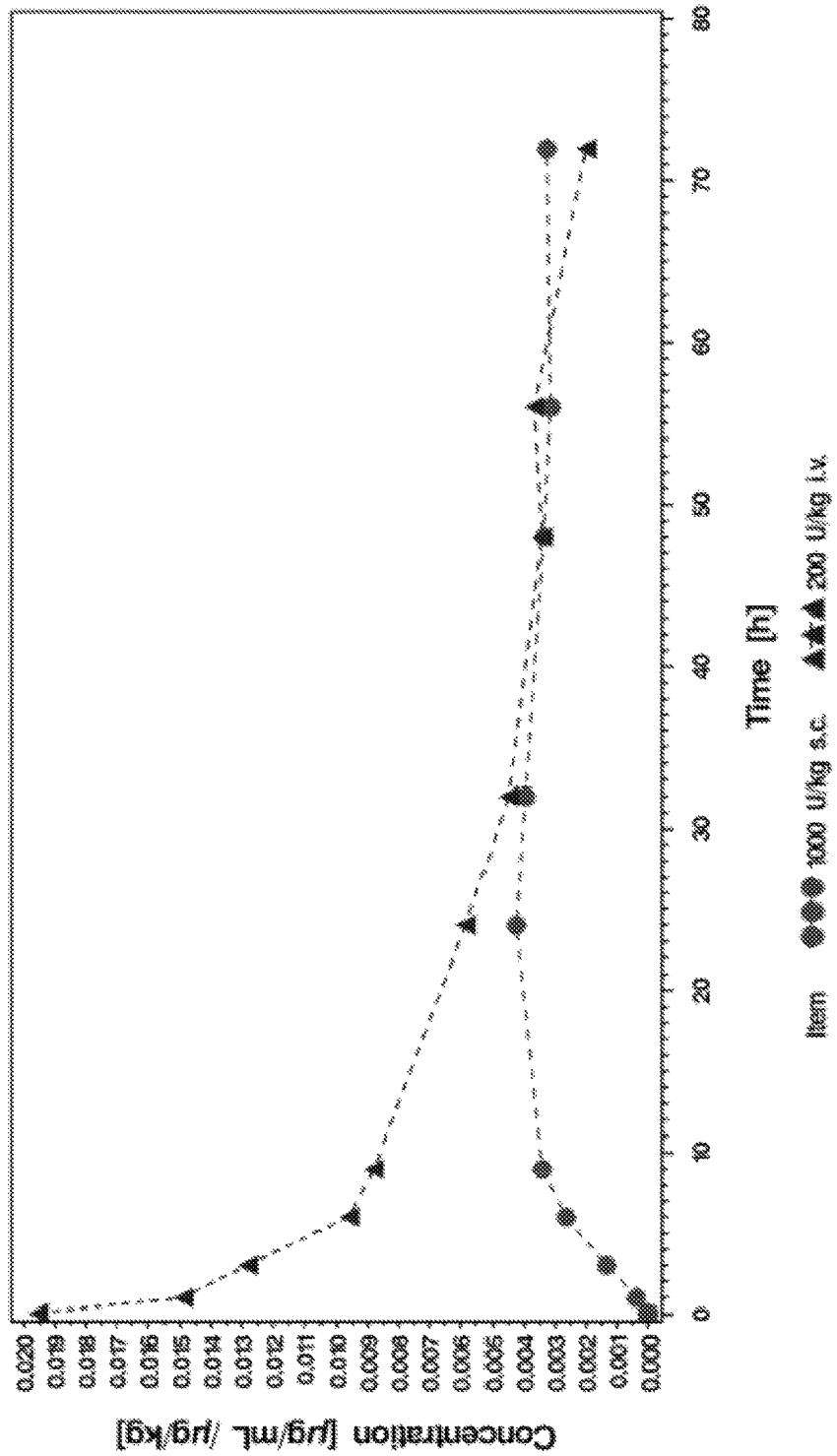
FIG. 2 shows the mean plasma concentrations of ADAMTS13 activity. Median $T_{max}$ after s.c. administration was 28 h for ADAMTS13 antigen

As expected, after i.v. administration the median $T_{max}$ (time to $C_{max}$) was 5 min, indicating immediate bioavailability. Median $T_{max}$ after s.c. administration was 24 h for ADAMTS13 activity and 28 h for ADAMTS13 antigen. Mean plasma concentrations of ADAMTS13 activity are summarized in FIG. 1 and the averaged concentrations of ADAMTS13 antigen are summarized in FIG. 2.

The dose-adjusted $AUC_{0-tlast}$ [h*U/mL/U/kg and h*m/mL/µg/kg] after i.v. administration was 0.306 for activity and 0.373 for antigen. $AUC_{0-tlast}$ was computed using the trapezoidal rule from time point 0 to the last sampling time ($t_{last}$) (Hauschke et al. 2007). The dose-adjusted $AUC_{0-tlast}$ following s.c. administration was 0.198 for activity and 0.243 for antigen. Thus, the ratio of the dose-adjusted $AUC_{0-tlast}$ following s.c. and i.v. administration was 0.646 for activity and 0.651 for antigen. IVR [%] was 55.8 (activity) and 79.3 (antigen) after i.v. administration and 13.8 (activity) and 17.3 (antigen) after s.c. administration.

Since the plasma level of rADAMTS13 did not decline sufficiently during the observation period, the estimation of the terminal and initial half-lives has to be viewed with caution. Thus, the dependent parameters (MRT, Vss, Cls, $AUC_{0-inf}$) may be unreliable as well. A follow-up study will be conducted to assess these parameters. Assessment of binding antibodies against rADAMTS13 was negative for all samples from all animals.

Results of the assessment of the minipigs' VWF multimer pattern were indicative for a very limited cleavage of endogenous VWF by recombinant ADAMTS13 (Table 3). The satellite band close to a low VWF-mer slightly increased in intensity over time in animals receiving s.c. administration, but not in animals receiving i.v. administration. The height of the VWF multimer patterns did not change in either group.

TABLE 3

Multimer analysis of recombinant ADAMTS13
from low and high resolution agarose gels.

| Experimental Group | No. of animals | VWF cleavage |
|---|---|---|
| Intravenous Group (200 IU/kg i.v.) | 1 | No |
| | 2 | No |
| | 3 | No |
| | 4 | No |
| Subcutaneous Group (1000 IU/kg s.c.) | 1 | Slight increase in one satellite band intensity |
| | 2 | Slight increase in one satellite band intensity |
| | 3 | Slight increase in one satellite band intensity |
| | 4 | Slight increase in one satellite band intensity |

Example 2: The Pharmacokinetic Properties of rADAMTS13 with Intravenous and Subcutaneous Administration This study was conducted to evaluate the pharmacokinetic properties of recombinant ADAMTS13 in Göttingen minipigs after intravenous (i.v.) or subcutaneous (s.c.) administration. In this study, 4 male Göttingen minipigs were administered i.v. ADAMTS13 (the "intravenous group") and 4 male Göttingen minipigs were administered s.c. ADAMTS13 (the "subcutaneous group").

The male Göttingen minipigs were acclimated to study procedures and anesthetized for catheter implantation as described in Example 1.

This study was a trial using 3 and 5 male Göttingen minipigs per group. Both groups received a nominal dose of 200 FRETS-U/kg rADAMTS13. Three animals were dosed i.v., the other five animals were dosed s.c. Blood was sampled via the central venous catheter before administration of the test item and 5 min, 1 h, 2 h, 6 h, 5 h, 23 h, 30 h, 47 h, 54 h, 71 h, 78 h, 95 h and 102 h after administration of the test item.

Blood samples were prepared as follows: The first 0.5-0.7 mL were discarded to avoid dilution with the catheter lock solution (saline). Then, 0.8 mL blood was collected and mixed with 0.2 mL sodium citrate. The blood sample was centrifuged with 5700 rpm (1×10 min, 1×5 min). The plasma was stored at <−60° C.

ADAMTS13 activity was determined by a FRETS assay and antigen by an ELISA.

Figure 3:
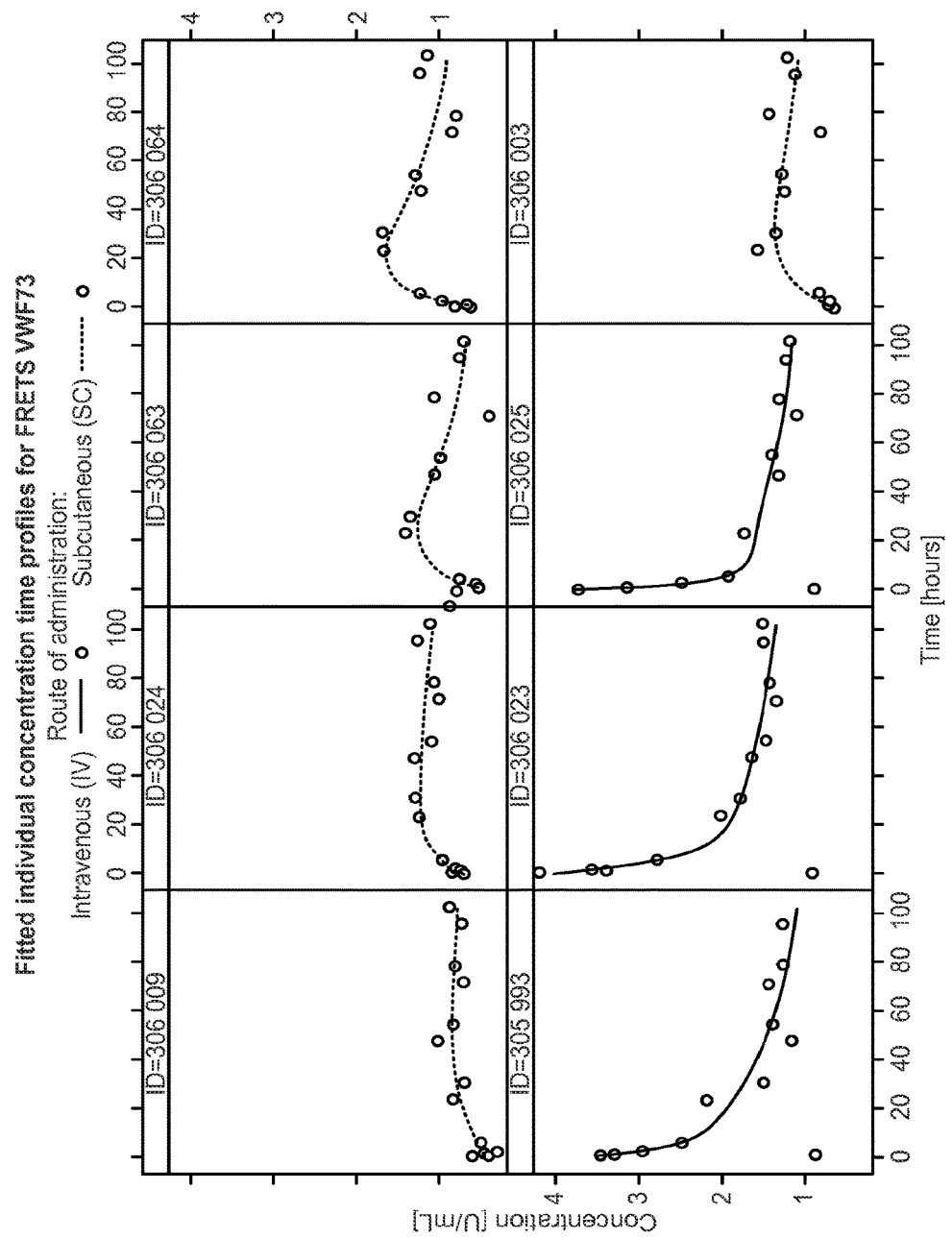
FIG. 3 shows observed (circles) and predicted concentrations (solid lines) for individual animals. Concentrations following i.v. administration were fitted using a two-compartmental model whereas concentrations following s.c. administration were fitted using a one-compartmental model with first-order absorption and first order elimination. Both models were modified by inclusion of an additional covariate to model the assumed constant endogenous ADAMTS13 activity.
Figure 4:
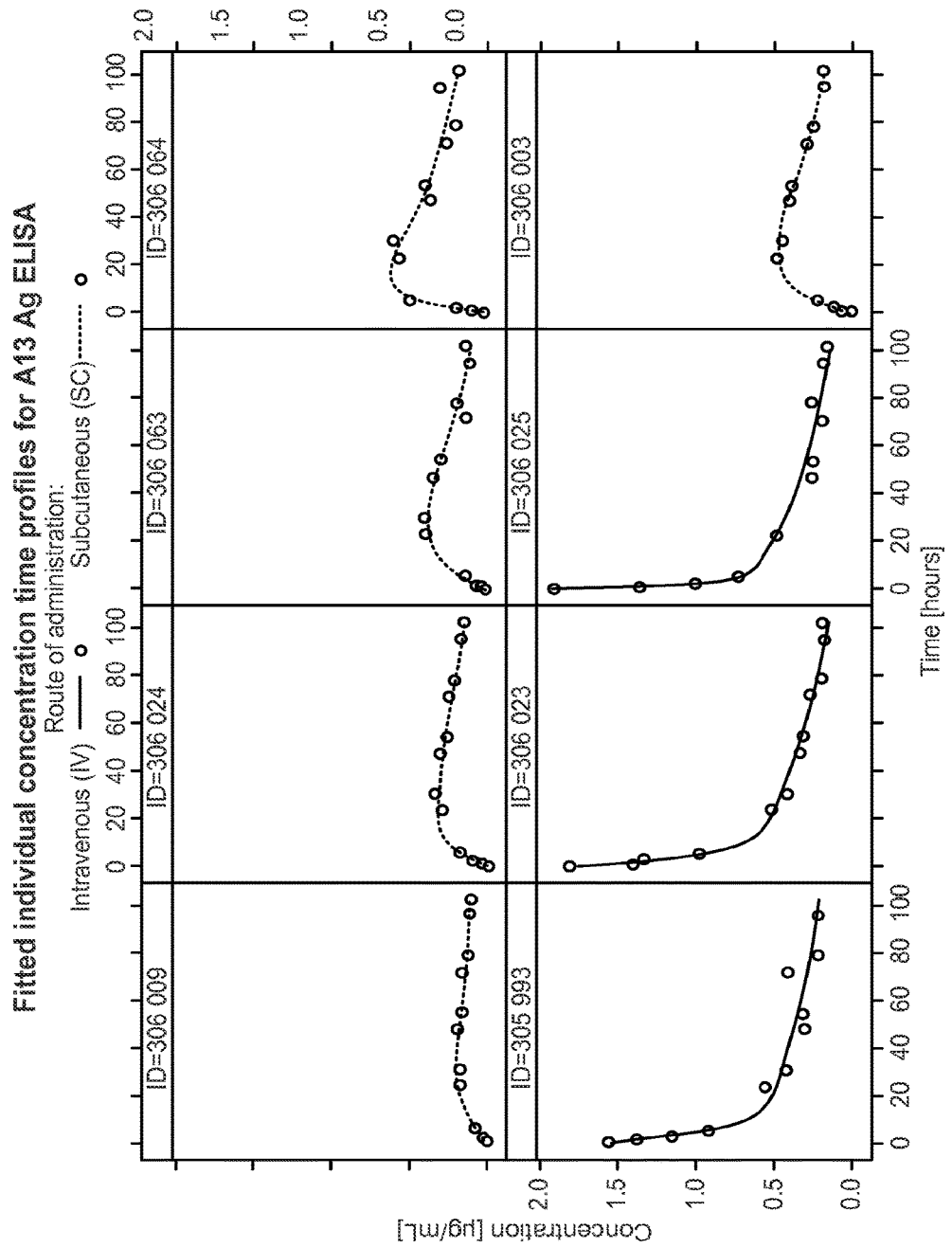
FIG. 4 shows the concentrations observed adjusted for borderline values and corresponding predicted concentrations for individual animals. Concentrations following i.v. administration were predicted using a two-compartmental model whereas concentrations following s.c. administration were predicted using a one-compartmental model with first-order absorption and first-order elimination.

As expected, after i.v. administration the median $T_{max}$ (time to $C_{max}$) was 5 min, indicating immediate bioavailability. Median $T_{max}$ after s.c. administration was 30 h. Mean plasma concentrations of ADAMTS13 activity are summarized in FIG. 3 and the averaged concentrations of ADAMTS13 antigen are summarized in FIG. 4.

The $AUC_{0-tlast}$ [U/mL/*h and µg/mL*h] after i.v. administration was 68.25 for activity and 39.81 for antigen. The $AUC_{0-tlast}$ following s.c. administration was 47.16 for activity and 26.23 for antigen. IVR [%] was 61.0 (activity) and 45.6 (antigen) after i.v. administration and 13.0 (activity) and 9.6 (antigen) after s.c. administration.

Terminal half-life [h] after i.v. administration was 46.96 for activity and 48.83 for antigen. Terminal half-life after s.c. administration was 56.76 for activity and 41.25 for antigen. MRT [h] was 64.08 (activity) and 66.26 (antigen) after i.v. administration and 104.2 (activity) and 77.52 (antigen) after s.c. administration.

In summary, the bioavailability of the s.c. administration relative to the i.v. administration was 65.9% and 69.1% for ADAMTS13 antigen and ADAMTS13 activity, respectively.

What is claimed is:

1. A method for treating a bleeding episode associated with an increase in blood clotting activity associated with a specific indication in a mammal, the method comprising subcutaneously administering a therapeutically effective amount of a composition comprising isolated a disintegrin and metalloproteinase with thrombospondin type I motifs 13 (ADAMTS13) to the mammal in need thereof, wherein the ADAMTS13 has a bioavailability of at least 40% after subcutaneous administration as compared to intravenous administration normalized for the same dose.

2. The method of claim 1, wherein the specific indication is inherited thrombotic thrombocytopenic purpura (TTP) and the standard intravenous dose is from about 10 to about 80 activity units per kilogram body weight.

3. The method of claim 1, wherein the specific indication is acquired TTP and the standard intravenous dose is from about 20 to about 1,000 activity units per kilogram body weight.

4. The method of claim 1, wherein the specific indication is myocardial infarction, ischemia reperfusion injury, or both and the standard intravenous dose is about 20-2000 activity units per kilogram body weight.

5. The method of claim 1, wherein the specific indication is cerebral infarction, ischemia reperfusion injury, or both and the standard intravenous dose is about 20-2000 activity units per kilogram body weight.

6. The method of claim 1, wherein the ADAMTS13 has a bioavailability of 50-80% after subcutaneous administration as compared to intravenous administration normalized for the same dose.

7. The method of claim 1, wherein the ADAMTS13 has a bioavailability of at least 50% after subcutaneous administration as compared to intravenous administration normalized for the same dose.

8. The method of claim 1, wherein the ADAMTS13 has a bioavailability of at least 55% after subcutaneous administration as compared to intravenous administration normalized for the same dose.

9. The method of claim 1, wherein the ADAMTS13 has a bioavailability of at least 60% after subcutaneous administration as compared to intravenous administration normalized for the same dose.

10. The method of claim 1, wherein the ADAMTS13 has a bioavailability of at least 65% after subcutaneous administration as compared to intravenous administration normalized for the same dose.

11. The method of claim 1, wherein the ADAMTS13 has a bioavailability of at least 70% after subcutaneous administration as compared to intravenous administration normalized for the same dose.

12. The method of claim 1, wherein the ADAMTS13 has a bioavailability of at least 75% after subcutaneous administration as compared to intravenous administration normalized for the same dose.

13. The method of claim 1, wherein the ADAMTS13 has a bioavailability of at least 80% after subcutaneous administration as compared to intravenous administration normalized for the same dose.

14. The method of claim 1, wherein the ADAMTS13 is administered in a single bolus injection monthly.

15. The method of claim 1, wherein the ADAMTS13 is recombinant.

16. The method of claim 1, wherein the ADAMTS13 is plasma derived.

17. The method of claim 1, wherein the mammal is a human.

18. The method of claim 1, wherein the composition is a stable aqueous solution ready for administration.

19. The method of claim 1, wherein the composition is lyophilized.

20. The method of claim 19, wherein the composition is reconstituted with a pharmaceutically acceptable vehicle suitable for injection.

21. The method of claim 1, wherein the specific indication is disseminated intravascular coagulation (DIC).

22. The method of claim 1, wherein the ADAMTS13 is administered in a single bolus injection every two weeks.

23. The method of claim 1, wherein the ADAMTS13 is administered in a single bolus injection weekly.

24. The method of claim 1, wherein the ADAMTS13 is administered in a single bolus injection twice a week.

25. The method of claim 1, wherein the ADAMTS13 is administered in a single bolus injection daily.

26. The method of claim 1, wherein the ADAMTS13 is administered in a single bolus injection every 12 hours.

27. The method of claim 1, wherein the ADAMTS13 is administered in a single bolus injection every 8 hours.

28. The method of claim 1, wherein the ADAMTS13 is administered in a single bolus injection every six hours.

29. The method of claim 1, wherein the ADAMTS13 is administered in a single bolus injection every four hours.

30. The method of claim 1, wherein the ADAMTS13 is administered in a single bolus injection every two hours.

\* \* \* \* \*